United States Patent [19]

Katoh et al.

[11] Patent Number: 5,221,599
[45] Date of Patent: Jun. 22, 1993

[54] SILVER HALIDE PHOTOGRAPHIC LIGHT SENSITIVE MATERIAL

[75] Inventors: Eisaku Katoh, Hachioji; Shuichi Sugita, Hino; Shuji Kida, Iruma, all of Japan

[73] Assignee: Konica Corporation, Tokyo, Japan

[21] Appl. No.: 703,745

[22] Filed: May 21, 1991

[30] Foreign Application Priority Data

May 23, 1990 [JP] Japan .................. 2-132867

[51] Int. Cl.$^5$ .............................. G03C 7/305
[52] U.S. Cl. ................... 430/544; 430/957; 430/558; 430/553; 430/555; 430/557
[58] Field of Search ......... 430/544, 957, 553, 555, 430/557, 558, 558 A

[56] References Cited

U.S. PATENT DOCUMENTS

| | | | |
|---|---|---|---|
| 4,409,323 | 10/1983 | Sato et al. | 430/543 |
| 4,500,633 | 2/1985 | Menjo et al. | 430/957 |
| 4,849,325 | 7/1989 | Sasaki et al. | 430/505 |
| 4,861,701 | 8/1989 | Burns et al. | 430/557 |

FOREIGN PATENT DOCUMENTS 0252376 1/1988 European Pat. Off. .
1164942 9/1989 Japan .

OTHER PUBLICATIONS

Patent Abstracts of Japan vol. 13, #436 (P-938)(3784) Sep. 29, 1989.

*Primary Examiner*—Charles L. Bowers, Jr.
*Assistant Examiner*—Martin Angebranndt
*Attorney, Agent, or Firm*—Finnegan, Henderson, Farabow, Garrett & Dunner

[57] ABSTRACT

A compound used as a silver halide photographic light sensitive material for releasing a photographically useful group (PUG) by the reaction with an oxidized developing compound during the developing process is disclosed.

The compound has several timing groups so that the releasing can be controlled by several steps of the reactions to meet a required timing.

The compound can be modified with various kinds of substituents so that the width of the reacting area is controlled.

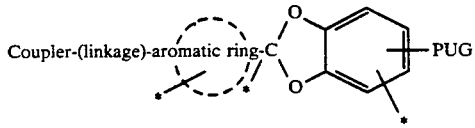

*substituent(s)

10 Claims, No Drawings

SILVER HALIDE PHOTOGRAPHIC LIGHT SENSITIVE MATERIAL

FIELD OF THE INVENTION

This invention relates to a silver halide photographic light sensitive material containing a novel coupler capable of releasing a photographically useful group.

BACKGROUND OF THE INVENTION

In photographic industry, there have so far been the known couplers each capable of releasing a photographically useful group upon reaction thereof with the oxidized product of a developing agent. The above-mentioned photographically useful groups include, for example, a development inhibitor, a development accelerator, a bleaching accelerator, a fogging agent, a dye, and a fluorescent whitening agent. The above-given photographically useful groups are able to contribute to an image improvement and an image stability, when they are released imagewise or non-imagewise into a silver halide emulsion layer. For example, U.S. Pat. Nos. 3,227,554 and 3,148,062, and Journal of the American Chemical Society, Vol. 72, 1950, p. 1533, disclose each the couplers capable of releasing a development inhibitor or a dye from the coupling position. And, U.S. Pat. No. 3,703,801 discloses the couplers each capable of releasing a bleaching accelerator from the coupling position after completing a reaction of the oxidized product of a developing agent with the couplers. Further, there have so far been the known compounds each incapable of producing any dyes, but capable of releasing a photographically useful group upon reaction thereof with the oxidized product of a developing agent. Among these compounds, the hydroquinone capable of releasing a development inhibitor is disclosed in, for example, U.S. Pat. No. 3,930,863.

For the above-mentioned photographically useful groups including, particularly, a development inhibitor and a bleaching accelerator, it has been well known that the time and positional controls of displaying the advantages of the photographically useful groups shall be essential for the improvements of an image sharpness and an image graininess. With the purpose of controlling the advantages thereof, the couplers each comprising a photographically useful group coupled to the active site through a timing group are disclosed in U.S. Pat. No. 4,248,962. Besides, Japanese Patent Publication Open to Public Inspection (hereinafter referred to as Japanese Patent O.P.I. Publication) Nos. 60-185950/1985 and 61 233741/1986 disclose the compounds each capable of releasing a photographically useful group, after the group is released from the active site of a coupler and then hydroquinone, catechol or pyrogallols each released thereby is then oxidation-reduction reacted successively with the oxidized product of a developing agent. In the compounds disclosed therein, however, the storage stability is poor and the unfavorable phenomenon is so produced as to be affected by an oxidation reaction before the coupler is to be reacted with the oxidized product of a developing agent. In this instance, when an aromatic compound is released, the readiness of the oxidation thereof shall of course be relative to the releasing speed, diffusing speed or its utility factor each of a photographically useful group. However, the readiness of the oxidation thereof may be controlled to some extent by adjusting the number of phenolic hydroxyl groups. In the second stage of the oxidation reaction of a compound substituted with a phenolic hydroxyl group in the position of a benzene ring, a desirable reaction speed may be obtained when 2 or 3 phenolic hydroxyl groups are substituted. In the form of releasing a photographically useful group from a conventional type coupler, there has raised a problem that a preserbavility is deteriorated by an air oxidation, because the hydroxyl group can protect only one coupler in the state where the hydroxyl group is coupled to the coupler. It may be expected that the deterioration of the preservability may be improved by protecting the phenolic hydroxyl group. However, the cleaving speed of a protective group has not been controlled in a procedure of hydrolyzing an ester bond, such as that disclosed in Japanese Patent O.P.I. Publication No. 61-230553/1986

Japanese Patent O.P.I. Publication No. 1-16494/1989 discloses the compounds each in which the hydroxyl group of a catechol is protected in the active site of a colorless coupler. However, those compounds have each a high pKa value in the active site position and incapable of releasing PUG sufficiently.

In the PUG-releasing couplers described in Japanese Patent O.P.I. Publication No. 1-154057/1989, the coupler reasing speed thereof was nothing but the same thing as in the conventional couplers capable of releasing PUG through a timing group.

SUMMARY OF THE INVENTION

It is an object of the invention to provide a silver halide photographic light sensitive material excellent in image sharpness, graininess, color reproducibility and desilvering property, which is prepared by making use of a novel coupler capable of displaying a storage stability and releasing a photographically useful group upon controlling the time and position of the photographically useful group.

DETAILED DESCRIPTION OF THE INVENTION

The above-mentioned object of the invention can be achieved with a silver halide photographic light sensitive material characterized in containing the compound represented by the following formula I:

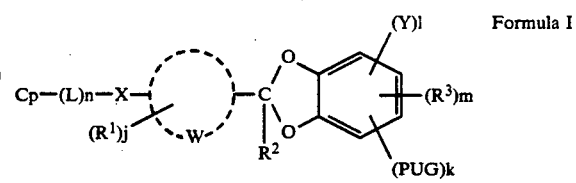

Formula I wherein Cp represents a coupler residual group from which a hydrogen atom in the active site thereof is removed; L represents a coupling group; n is an integer of 0 or 1; $R^1$, $R^2$ and $R^3$ represent each a hydrogen atom or a substituent; W represents an aromatic ring having a 5- or 6-membered ring or a heterocyclic ring; j represents an integer of 0 to 4; PUG represents a photographically useful group; l represents an integer of 0 or 1; m and k represent each an integer of 0 to 4, provided, l+m+k represents an integer of not more than 4; X represents a divalent coupling group; and Y represents a substituent capable of coupling to a benzene ring through a hetero atom.

The couplers represented by Formula I are each capable of releasing PUG in accordance with the following reaction scheme:

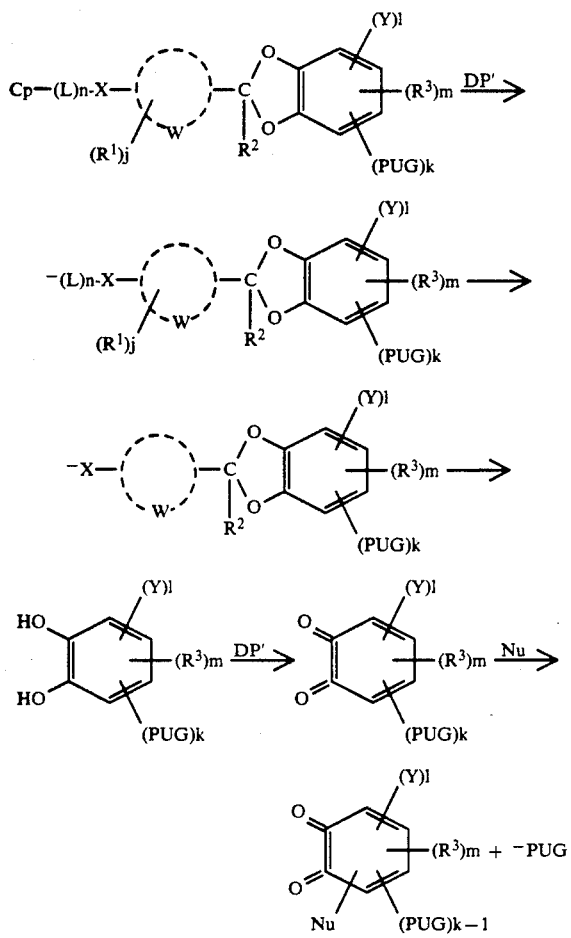

wherein Cp, $R^1$, $R^2$, $R^3$, j, k, l, m, n, and W are synonymous with those described in Formula I; DP' represents an oxidized product of an aromatic primary amine developing agent; and Nu represents a nucleophilic reactive seed made present in a developing bath, such as a hydroxide ion and a sulfurous acid ion. In the course from the point of time when the groups following L are released in the first stage of the reaction with the oxidized product of a developing agent of the invention to the point of time when a photographically useful group is released, there produce many steps of reactions such as the desorption protection of a catechol hydroxyl group, the oxidation of the catechols and the reaction of addition desorption produced with a nucleophilic material, so that there may be an appropriate time interval until the photographically useful group can display its effect and the photographically useful group can suitably be diffused in an emulsion layer. It is the matter of course that the speed of the second staged oxidation reduction depends on the concentration of the oxidized product of the developing agent and, therefore, the smaller an exposure quantity, the longer a diffusion distance, so that an interlayer effect can be more displayed. On the other hand, the catechols produced therein are protected by their own hydroxyl groups in the sate where they are coupled to couplers and, therefore, the oxidation reduction is strongly reacted and the preservability can also be excellent. Further, the cleaving reaction can be stabilized in preservation and can also be progressed smoothly when the catechols are released from the couplers.

Now, the above-given formula I will be further detailed below.

Coupler residual group Cp may be any groups, provided, they are capable of releasing any groups following coupling groups L upon reaction with a oxidized developing agent. The coupler residual groups Cp include, for example, those applicable to an ordinary dye-formable coupler producing a coloring product upon reaction with an oxidized developing agent, and the coupler groups each capable of producing a colorless product upon reaction with an oxidized color developing agent. These two type of couplers are well known in the skilled in the art. The coupler residual groups may be either stabilized or not stabilized. They may also be those of monomer, dimer, oligomer, or polymer. The groups following L are coupled to a coupler residual group in either one of the positions where the groups released from a coupler upon reaction with an oxidized developing agent can be coupled. Among the coupler residual groups each represented by Cp, the typical examples of yellow coupler residual groups are described in U.S. Pat. Nos. 2,298,443, 2,407,210, 2,875,057, 3,048,194, 3,265,506 and 3,447,928; and Farbkupplereine Literaturuversiecht Agfa Mitteilung (Band II), pp. 112–126, 1961. Among the yellow coupler residual groups, acylacetanilides including, for example, benzoylacetanilide and pyvaloylacetanilide may preferably be used.

The typical examples of the magenta coupler residual groups are described in U.S. Pat. Nos. 2,369,489, 2,343,703, 2,311,182, 2,600,788, 2,908,573, 3,062,653, 3,152,896, 3,519,429, 3,725,067 and 4,540,654; Japanese Patent O.P.I. Publication No. 59-162548/1984; and the above-given Farbkupplereine Literaturuversiecht Agfa Mitteilung (Band II), pp. 126–158, 1961. Among these magenta coupler residual groups, pyrazolone or pyrazoloazole (such as pyrazolotriazole and pyrazoloimidazole) may preferably be used.

The typical examples of the cyan coupler residual groups are described in U.S. Pat. Nos. 2,367,531, 2,423,730, 2,474,293, 2,772,162, 2,395,826, 3,002,836, 3,034,892, 3,041,236 and 4,666,999; and the above-given Farbkupplereine Literaturuversiecht Agfa Mitteilung (Band II), pp. 156–175, 1961. Among these cyan coupler residual groups, phenols and naphthols may preferably be used.

The typical examples of the coupler residual groups each capable of producing a substantially colorless product are described in British Patent No. 861,138; and U.S. Pat. Nos. 3,632,345, 3,928,041, 3,958,993 and 3,691,959. Among these coupler residual groups, a cyclic carbonyl compound may preferably be used.

The coupling groups each represented by L are each a group capable of releasing a group following X from Cp under a time control. These groups may contain a group capable of controlling the speed of the reaction of Cp with the oxidized product of a developing agent, the speed of the diffusion of a group following X released from Cp, and the speed of releasing the group following X. The examples of these coupling groups include, typically, those capable of releasing a group following X upon making an intramolecular nucleophilic substitution reaction, which are disclosed in U.S. Pat. No. 4,248,962 and Japanese Patent O.P.I. Publication No.

57-56837/1982; those capable of releasing a group following X upon making an electron transfer reaction produced along a conjugated chain, which are described in Japanese Patent O.P.I. Publication Nos. 56-114946/1981 and 57-154234/1982; and, besides, the coupling groups disclosed in Japanese Patent O.P.I. Publication Nos. 57-188035/1982, 58-98728/1983, 59-206834/1984, 60-7429/1985, 60-214358/1985, 60-225844/1985, 60-229030/1985, 60-233649/1985, 60-237446/1985 and 60-237447.

As for the yellow coupler residual groups each represented by Cp denoted in Formula I, the groups represented by the following formulas II and III may preferably be used.

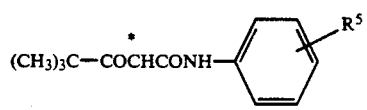

Formula II

Formula III

In the above-given formulas II and III, $R^5$ and $R^6$ represent each an alkyl group, a cycloalkyl group, an aryl group, a heterocyclic ring or a halogen atom; provided, the above-given alkyl, cycloalkyl and aryl groups and, heterocyclic ring may be coupled through an oxygen, nitrogen or sulfur atom. Also, the alkyl, cycloalkyl and aryl and heterocyclic ring may be coupled through a coupling group such as those of acylamino, carbamoyl, sulfonamido, sulfamoyl, sulfamoylcarbonyl, carbonyloxy, oxycarbonyl, ureido, thioureido, thioamido, sulfone and sulfonyloxy groups. The above-given alkyl, cycloalkyl and aryl and heterocyclic ring may further have a substituent such as a halogen atom, and a nitro, cyano, alkyl, alkenyl, cycloalkyl, aryl, alkoxy, aryloxy, alkoxycarbonyl, aryloxycarbonyl, carboxy, sulfo, sulfamoyl, carbamoyl, acylamino, ureido, urethane, sulfonamido, heterocyclic, arylsulfonyl, alkylsulfonyl, arylthio, alkylthio, alkylamino, anilino, hydroxy, imido, or acyl group.

When there are not less than two of $R^5$ and $R^6$, they may be the same with or the different from each other.

As for the magenta coupler residual groups represented by Cp denoted in Formula I, those represented by the following formulas IV, V, VI and VII may preferably be used.

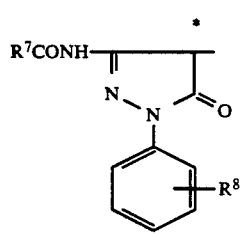

Formula IV

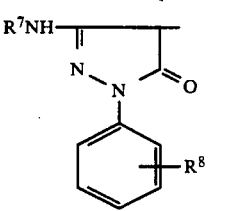

Formula V

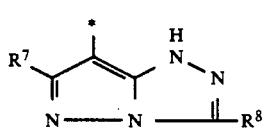

Formula VI

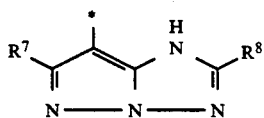

Formula VII

In the above-given formulas IV through VII, $R^7$ and $R^8$ are synonymous with $R^5$ and $R^6$ denoted in formulas II and III.

As for the cyan coupler residual groups represented by Cp denoted in formula I, those represented by the following formulas VIII, IX and X may preferably be used.

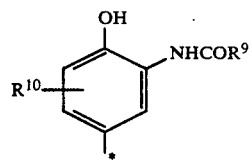

Formula VIII

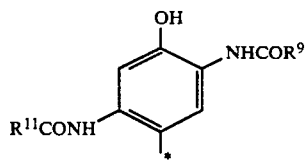

Formula IX

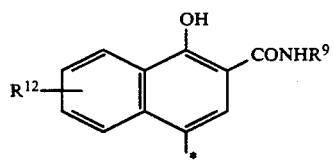

Formula X

In the above-given formulas VIII through X, $R^9$, $R^{10}$, $R^{11}$ and $R^{12}$ are each synonymous with $R^5$ and $R^6$ denoted in formulas II and III.

As for the coupler residual groups each capable of producing a substantially colorless coupler, which are represented by Cp denoted in Formula I, those represented by the following formulas XI through XIV may preferably be used.

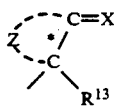

Formula XI wherein $R^{13}$ represents a hydrogen atom, an alkyl group, an aryl group, a halogen atom, an alkoxy group, an acyloxy group, or a heterocyclic group; X represents an oxygen atom or $=N-R^{14}$ in which $R^{14}$ represents an alkyl group, a hydroxy group, an alkoxy group, or a sulfonyl group; and Z represents a group consisting of non-metal atoms necessary to form a 5- to 7-membered ring (such as indanone, cyclopentanone and cyclohexanone) or a heterocyclic ring (such as piperidone, pyrrolidone and hydrocarbostyryl).

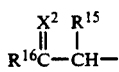  Formula XII wherein $R^{15}$ and $X^2$ are each synonymous with $R^{13}$ and X each denoted in Formula XI, respectively; and $R^{16}$ represents an alkyl group, an aryl group, a heterocyclic group, a cyano group, a hydroxy group, an alkoxy group, an aryloxy group, a heterocyclic-oxy group, an alkylamino group, a dialkylamino group or an anilino group.

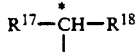  Formula XIII wherein $R^{17}$ and $R^{18}$ may be the same with or the different from each other and represent each an alkoxycarbonyl group, a cabamoyl group, an acyl group, a formyl group, a sulfonyl group, a sulfinyl group, a sulfamoyl group, an ammonium-mil group, or

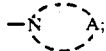

represents a group consisting of non-metal atoms necessary to form a 5- to 7-membered ring (such as phthalimide, triazole and tetrazole), in association with a nitrogen atom.

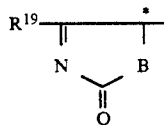  Formula XIV wherein $R^{19}$ represents an alkyl group, an aryl group, an anilino group, an alkylamino group or an alkoxy group; and B represents an oxygen atom, a sulfur atom or a nitrogen atom.

As for L useful for the invention, those represented by the following formulas XV, XVI and XVII may be included. It is, however, to be understood that L shall not be limited thereto.

  Formula XV wherein $W_1$ represents a group consisting of the atoms necessary to complete a benzene ring or a napthalene ring each allowed to have a substituent; $Y^1$ represents $-O-$, $-S-$ or $-NR^{22}-$ each coupled to the coupling position of a coupler residual group represented by Cp denoted in Formula I; $R^{21}$ and $R^{22}$ represent each a hydrogen atom, an alkyl group or an aryl group; and

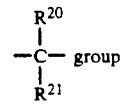 group is substituted to $Y^1$ in the ortho or para position so as to be coupled to X.

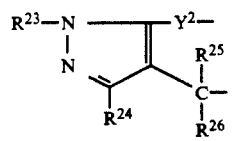  Formula XVI wherein $Y^2$, $R^{25}$ and $R^{26}$ are each synonymous with $Y^1$, $R^{20}$ and $R^{21}$ each denoted in Formula XV, respectively; $R^{23}$ represent a hydrogen atom, an alkyl group, an aryl group, an acyl group, a sulfonyl group, an alkoxycarbonyl group or a heterocyclic residual group; and $R^{24}$ represents a hydrogen atom, an alkyl group, an aryl group, a heterocyclic residual group, an alkoxy group, an amino group, an acid-amido group, a sulfonamide group, a carboxy group, an alkoxycarbonyl group, a carbamoyl group or a cyano group. Similar to the case of Formula XV, in the case of this coupling group, a

group is coupled to X in the coupling position $Y^2$ of the coupler residual group represented by Cp denoted in Formula I.

Next, the examples of the coupling groups each capable of releasing a group following X upon making an intramolecular nucleophilic substitution reaction will be given by the following formula XVII:

  Formula XVII wherein Nu represents a nucleophilic group having a rich electron containing oxygen, sulfur or nitrogen atom, and Nu is coupled to a coupler residual group represented by Cp denoted in Formula I in the coupling position thereof; E represents an electrophilic group having an insufficient electron containing carbonyl, thiocarbonyl, phosphinyl or thiophosphinyl group, and E is coupled to X; and Z represents a coupling group capable of relating both Nu and E in three-dimension to each other and releasing a group following X upon receipt of an interamolecular nucleophilic reaction from which the production of a 3- to 7-membered ring is derived after releasing Nu from a coupler residual group represented by Cp denoted in Formula I.

In Formula I, PUG represents a photographically useful group including, for example, a development inhibitor, a development accelerator, a bleaching accelerator, a fogging agent, a dye or a fluorescent whitening agent. When PUG represents a development inhibitor, the desirable PUGs include, for example, a phenyltetrazolylthio group, a 1,3,4-thiadiazolyl-2-thio group, a 1,3,4-oxadiazolyl-2-thio group, a 1,3,4-triazolyl-2-thio group, a benzoimidazolyl-2-thio group, a benzoxazolyl-2-thio group, a benzothiazolyl-2-thio group, a banzimidazolyl group or an imidazolylthio group. The above-given groups are allowed to have any desired substituents each substitutable to any substitutable positions.

In Formula 1, $R^1$ represents a hydrogen atom or a substituent. When j is not less than 2, each of $R^1$ can represent the same group or the different groups. When $R^1$ represents a substituent, the substituents include, for example, a halogen atom, an alkyl group (such as a methyl group or an ethyl group), an aryl group (such as a phenyl group, a p-anisyl group or a naphthyl group), a heteroaryl group (such as a pyridyl group or a thiazolyl group), an alkoxyl group (such as a methoxyl group or an ethoxyl group), an amino group, an alkylamino group (such as a dimethylamino group, a di(hydroxyethyl)amino group, an acetoxyethylamino group and a cyanoethylamino group), an alkylcarbamoyl group, an arylcarbamoyl group, an acylamino group, an allylamino group, a ureido group, a sulfonylamino group (such as a methylsulfonylamino group and a phenylsulfonylamino group), a nitro group, a cyano group, an alkylsulfonyl group (such as a methylsulfonyl group and a butylsulfonyl group), an arylsulfonyl group (such as a phenylsulfonyl group and a p-tolylsulfonyl group), an alkoxycarbonyl group (such as a methoxycarbonyl group and an ethoxycarbonyl group), an aryloxycarbonyl group (such as a phenoxycarbonyl group and a p-chlorophenoxycarbonyl group), an alkoxysulfonyl group, and an aryloxysulfonyl group. The substituents at issue shall not be limited to the above-given substituents.

In Formula I, $R^2$ represents a hydrogen atom or a substituent including, for example, an alkyl group, an aryl group or an acyl group.

In Formula I, $R^3$ represents a hydrogen atom or a substituent, provided that, when m is not less than 2, each of $R^3$ may represent the same group or the different groups. The substituents represented by $R^3$ include, for example, a halogen atom, an alkyl group (such as a methyl group and an ethyl group), an aryl group (such as a phenyl group, a p-anisyl group, and a naphthyl group), a heteroaryl group (such as a pyridyl group and a thiazolyl group), an alkoxyl group (such as a methoxyl group and an ethoxyl group), an amino group, an alkylamino group (such as a dimethylamino group and a di(hydroxyethyl)amino group, an acetoxyethylamino group and a cyanoethylamino group), an alkylcarbamoyl group, an arylcarbamoyl group, an acylamino group, an arylamino group, a ureido group, a sulfonylamino group (such as a methylsulfonylamino group and a phenylsulfonylamino group), a nitro group, a cyano group, an alkylsulfonyl group (such as a methylsulfonyl group and a butylsulfonyl group), an arylsulfonyl group (such as a phenylsulfonyl group and a p-tolylsulfonyl group) an alkoxycarbonyl group (such as a methoxycarbonyl group and an ethoxycarbonyl group), an aryloxycarbonyl group (such as a phenoxycarbonyl group and a p-chlorophenoxycarbonyl group), an alkoxysulfonyl group, and an aryloxysulfonyl group. However, the substituents represented by $R^3$ shall not be limited to the above-given substituents. Among the substituents, a nitro group, a cyano group, a sulfamoyl group, an alkylsulfamoyl group, and an arylsulfamoyl group may preferably be used, and a carbamoyl group, an alkylcarbamoyl group, an arylcarbamoyl group, an alkyloxycarbonyl group, an aryloxycarbonyl group and a carboxyl group may more preferably be used.

In Formula I, W represents a group capable of forming a 5- or 6-membered aromatic ring. These aromatic rings may have a condensed ring. The preferable ring systems include, for example, those of benzene, naphthalene, pyridine, pyrimidine pyrazole, imidazole, oxazole, thiazole, isoxazole, isothiazole, furan, thiophene, indole, benzofuran and benzothiophene, to which W shall not be limited.

In Formula I, Y represents a substituent coupled to a benzene ring through a heteroatom. The examples thereof include, preferably, a hydroxyl group, an alkoxyl group (such as an ethoxyl group and a methoxyl group), an amino group, an alkylamino group (such as a methylamino group and a di(2-cyanoethyl)amino group), a sulfonylamino group (such as a methanesulfonylamino group p-tolyl sulfonylamino), an acylamino group (such as an acetylamino group and a benzoylamino group), a sulfamoylamino group, an alkylsulfamoylamino group, and an arylsulfamoylamino group. Among them, the particularly preferable substituents include, for example, a hydroxyl group.

The typical examples of the couplers of the invention represented by Formula I will be given below. It is, however, to be understood that the invention shall not be limited thereto.

Exemplified Couplers

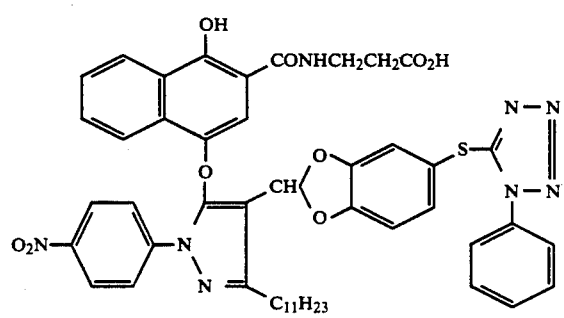

-continued
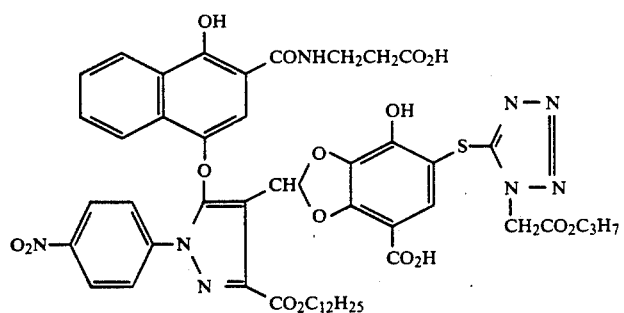
(2)
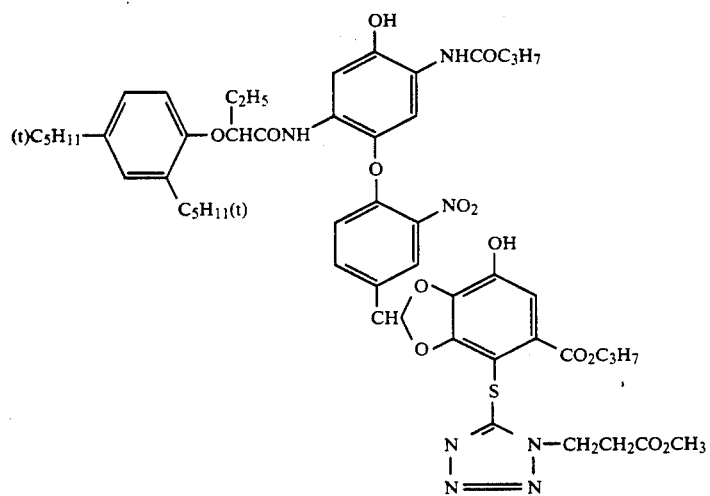
(3)
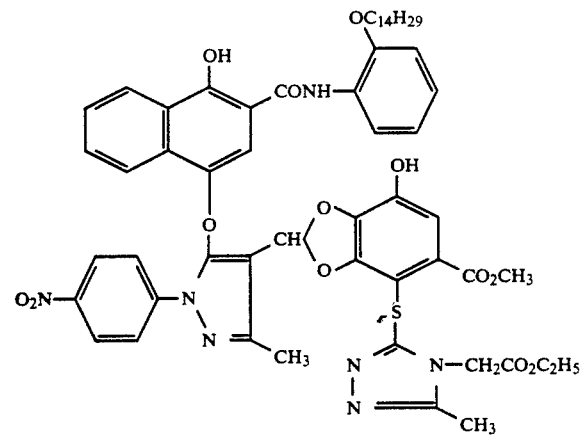
(4)

-continued
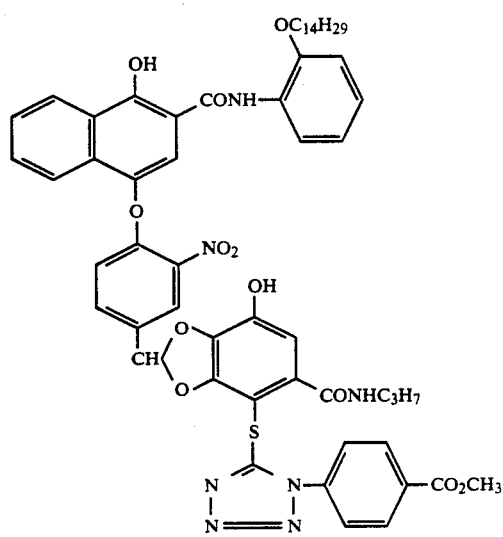
(5)
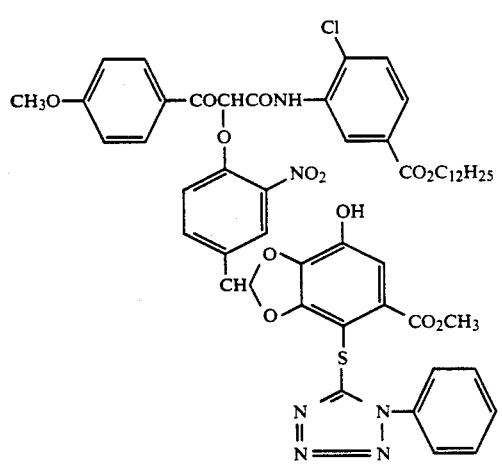
(6)
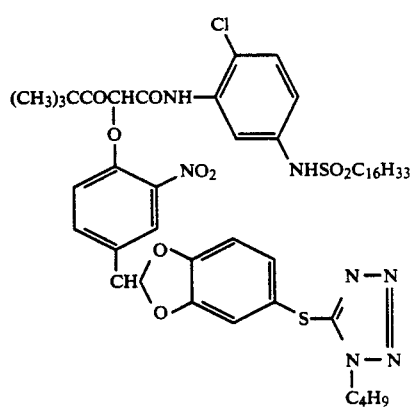
(7)

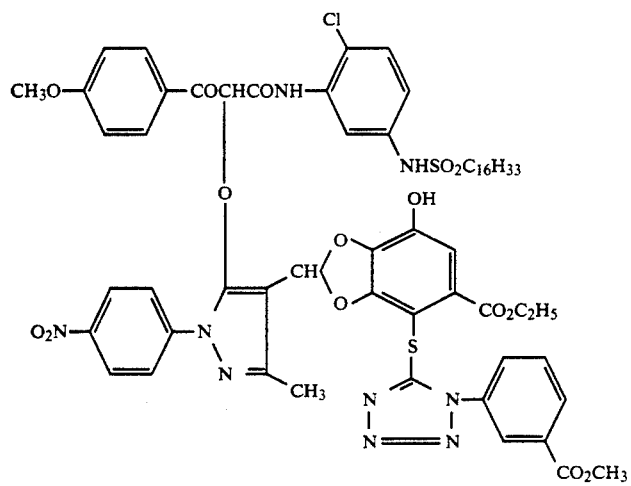
(8)
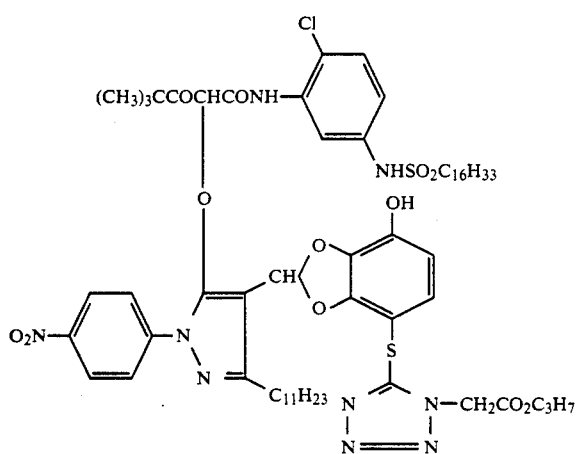
(9)
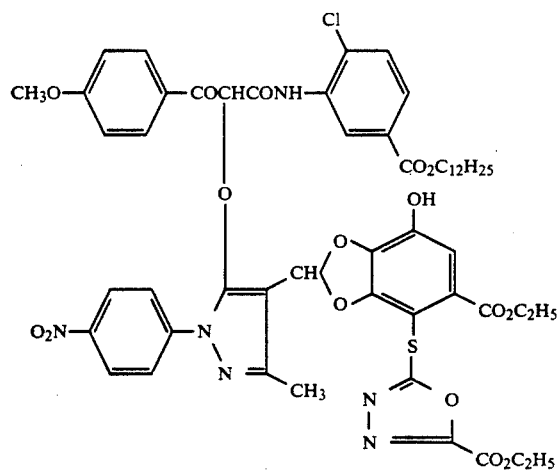
(10)

-continued
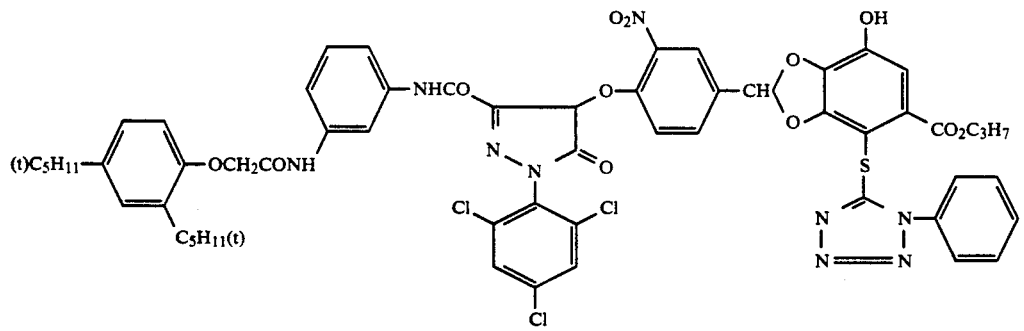 (11)
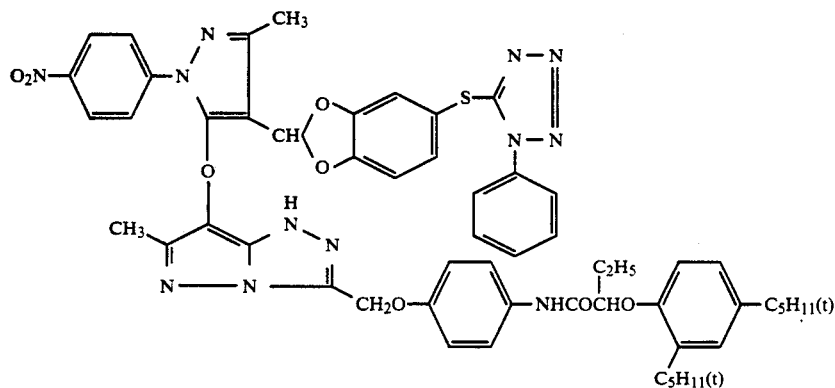 (12)
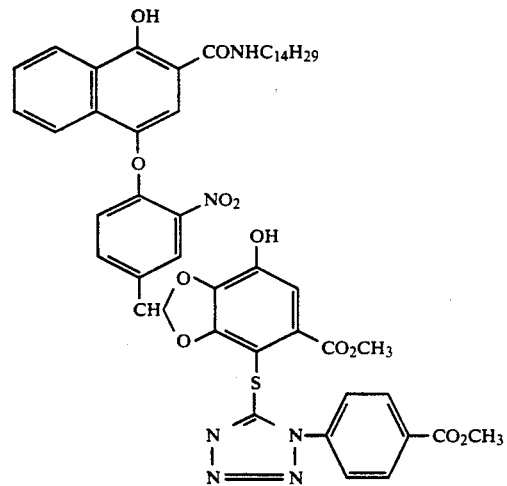 (13)
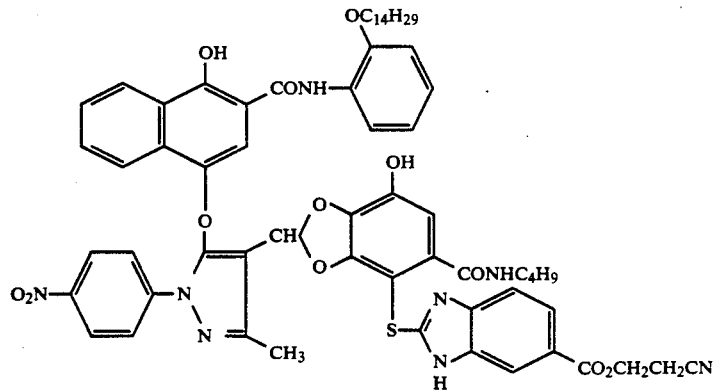 (14)

-continued
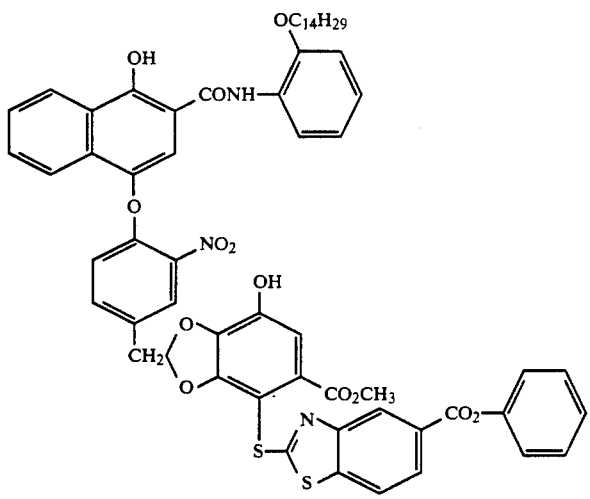
(15)
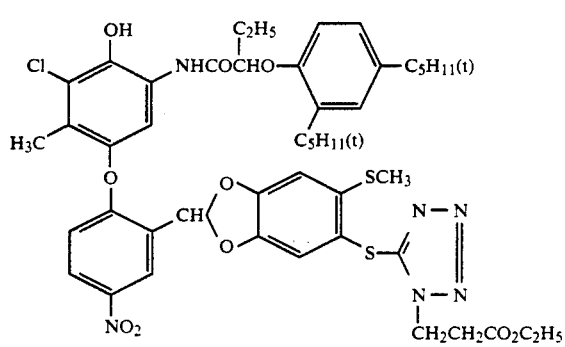
(16)
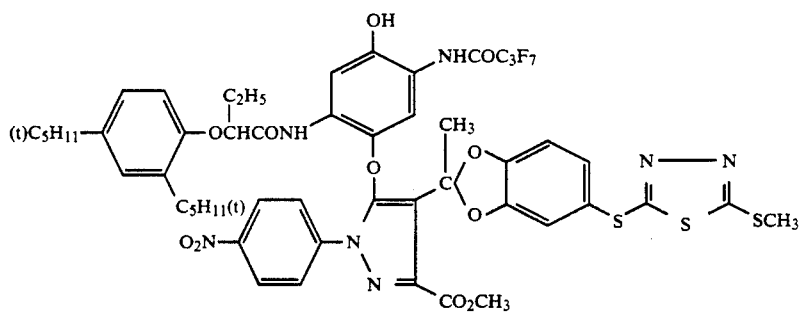
(17)
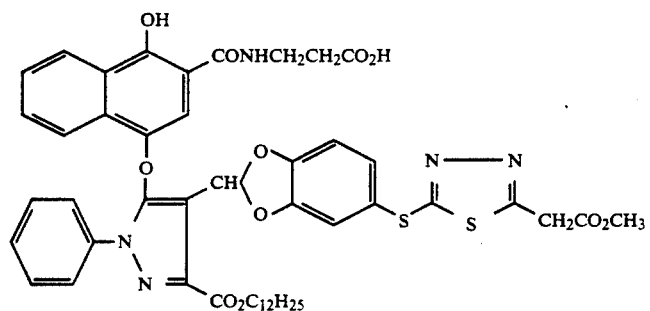
(18)

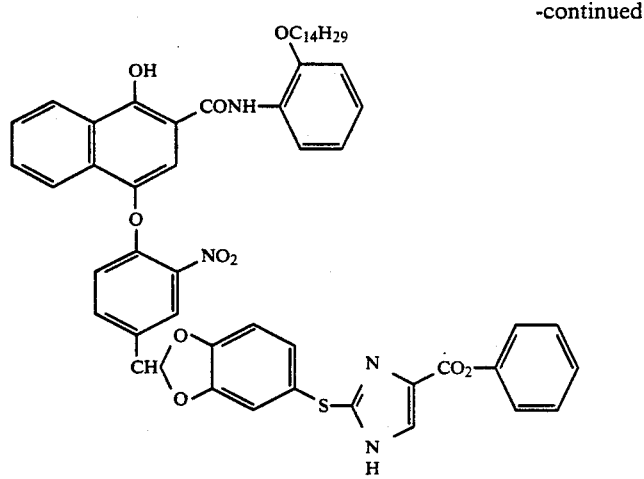
(19)
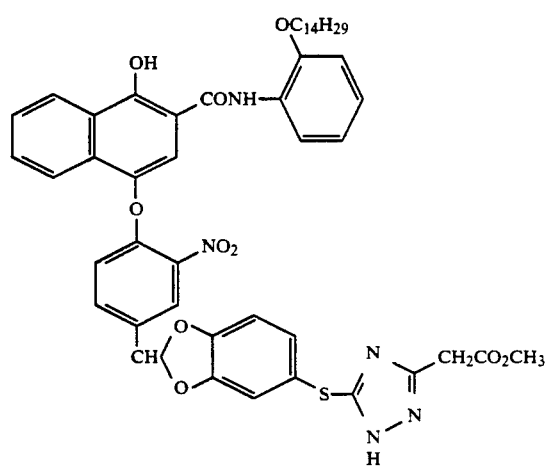
(20)
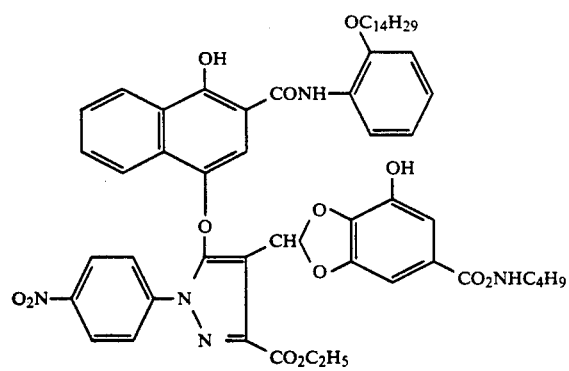
(21)
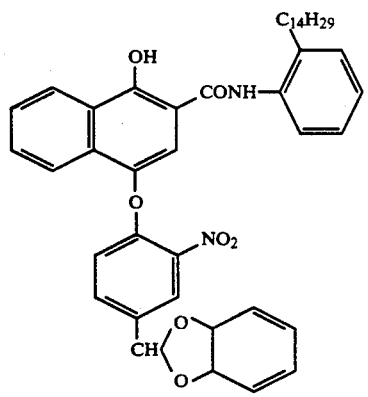
(22)

-continued
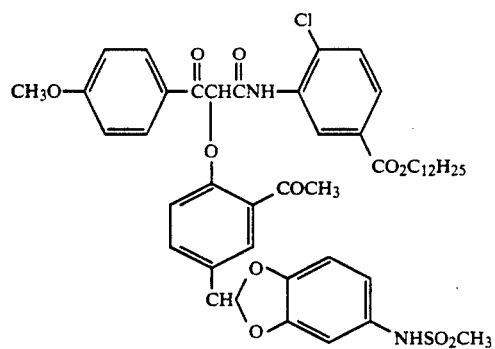
(23)
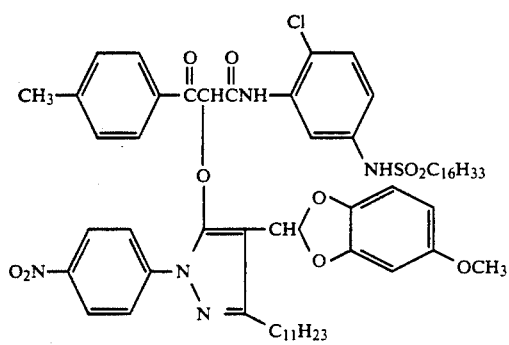
(24)
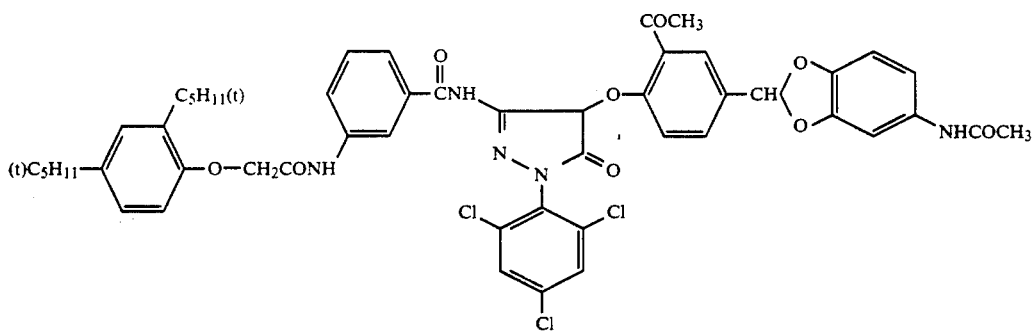
(25)
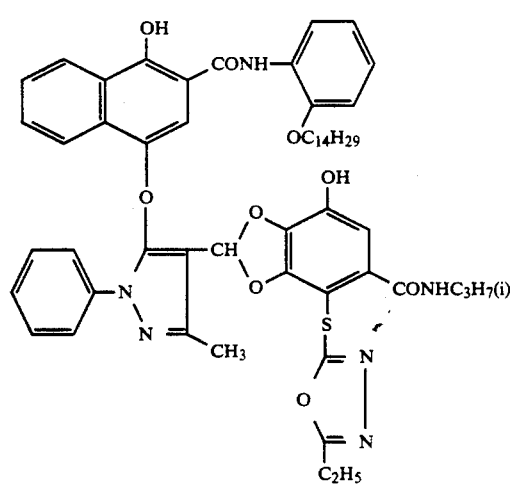
(26)

-continued
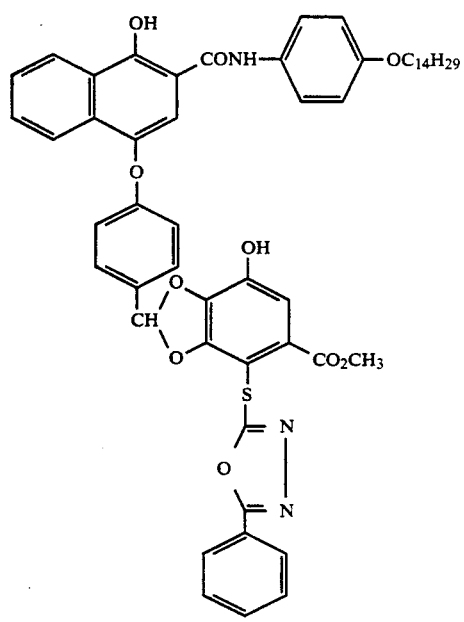
(27)
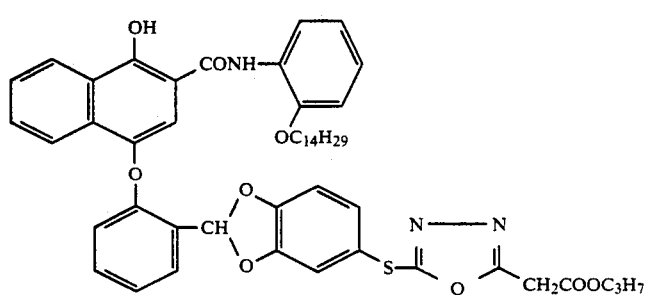
(28)
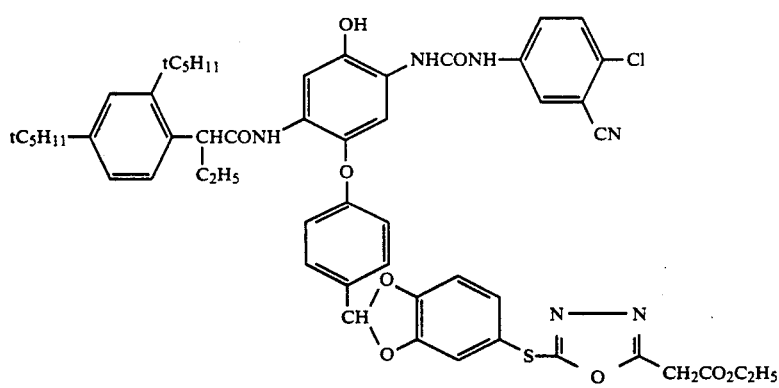
(29)
The couplers of the invention can be prepared in the processes which have been known in the industry of organic syntheses. The typical examples of the syntheses will be given below.
Synthesis Examples

Synthesis of Exemplified Compound 5

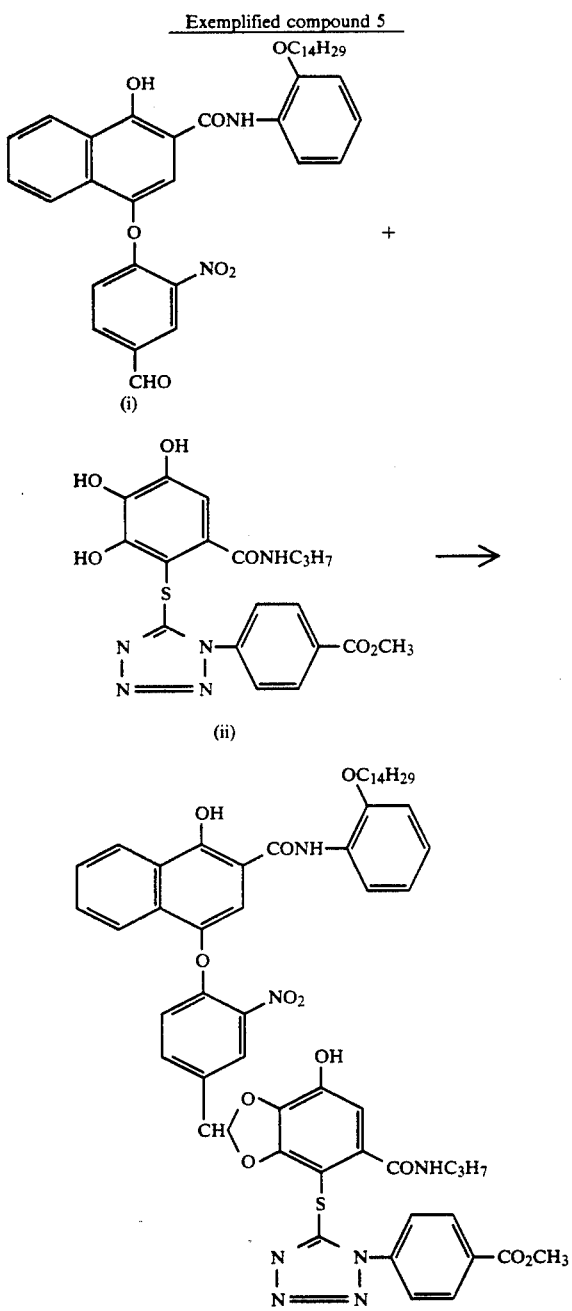

The above-given compounds, (i) of 6.41 g and (ii) of 4.45 g, were each dissolved in 150 ml of toluene and 0.10 g of p-toluenesulfonic acid was then added. The resulting solution was heated and reduced for 16 hours while removing water produced. After completing the reaction, the reactant was washed with a 0.1N $NaHCO_3$ solution and was then washed with water. After drying it with an anhydrous magnesium sulfate, the remaining toluene was distilled off under reduced pressure. The resulting oily matter was subjected to a silica gel column chromatography, so that 6.9 g of exemplified compound 5, that was in the form of colorless crystals, could be obtained.

The structure of the resulting compound was confirmed in NMR and Mass spectroscopic observations.

The couplers of the invention can be contained in a photographic light sensitive material and/or a photographic processing solution such as a developer and, inter alia, they may be contained preferably in a photographic light sensitive material.

The photographic light sensitive material may be either a single element comprising a support provided thereon with only one silver halide emulsion layer or a multilayered and multicolored element.

The couplers of the invention are each capable of produce a bimolecular type dye upon reaction of the coupler with the oxidized products of a color developing agent produced by developing silver halide in a silver halide emulsion layer. The silver halide emulsion layers may also contain the other photographic couplers such as an ordinary dye-forming coupler capable of forming a dye in an allied color, an inhibitor-releasable coupler and a masking coupler, as well as the couplers of the invention. The typical photographic light sensitive materials are those comprising each a support containing the following color light sensitive silver halide emulsion units; namely, a red color light sensitive silver halide emulsion unit containing not less than one kind of cyan dye-forming couplers, a green light sensitive silver halide emulsion layer unit containing not less than one kind of magenta dye-forming couplers, and a blue light sensitive silver halide emulsion layer unit containing not less than one kind of yellow dye-forming couplers.

Each of the above-mentioned silver halide emulsion layer units may also be comprised of not less than 2 layers each of which may further allowed to contain the other photographic coupler such as the above-mentioned couplers applicable to the industry.

For satisfying the characteristic requirements for the light sensitive materials, the couplers of the invention and other various couplers, each applicable to the invention, may be used in combination in one and the same layer, or the same compounds may also be introduced into each of not less than 2 kinds of the different layers.

The couplers of the invention may desirably be added in an amount within the range of $2 \times 10^{-5}$ to $1 \times 10^{-3}$ mols per sq. meter of a layer to be added.

When maing combination use of a coupler capable of forming an allied color, the coupler may desirably be added in an amount within the range of 0.001 to 20 mols per mol of the coupler of the invention.

The couplers applicable to the invention can be introduced into a light sensitive material in any one of a variety of the known dispersion processes. The examples of the processes include, typically, a solid dispersion process, an alkali dispersion process; desirably, a latex dispersion process and, preferably, a oil drop-in-water dispersion process. In the oil drop-in-water dispersion process, the couplers are dissolved in a single solution of either one of a high boiling organic solvent having a boiling point of not lower than 175.C or a low boiling organic solvent, or in a mixture of the both solvents, and the couplers are then finely dispersed in an aqueous medium such as water or an aqueous gelatin solution, in the presence of a surface active agent. The examples of the high boiling organic solvents are given in U.S. Pat. No. 2,322,027 and so forth. For carrying out such a dispersion as mentioned above, a layer inversion may be accompanied and, if required, the resulting dispersion may be used in a coating step after an auxiliary solvent is removed or reduced in a distillation, noodle-washing or ultrafiltration treatment.

As for the binders or protective colloids each applicable to the emulsion layers and interlayers of the photographic light sensitive materials of the invention, gelatin may advantageously be used. Any other hydrophilic colloids than the above-mentioned gelatin may also be used independently or in combination with the gelatin.

The photographic emulsion layer of the photographic light sensitive materials of the invention may contain any one of silver halides such as silver bromide, silver iodobromide, silver iodochlorobromide, silver chlorobromide and silver chloride. The desirable silver halide applicable to a color photographic material for photographic use is silver iodobromide or silver iodochlorobromide, each containing silver iodide in a proportion of not more than about 15 mol % and, preferably, silver iodobromide containing silver iodide in a proportion within the range of about 2 mol % to about 12 mol %. The desirable silver halide applicable to a photographic light sensitive material is silver bromide, silver chlorobromide or silver iodochlorobromide.

The silver halide grains contained in photographic emulsions may be the so-called regular grains comprising the crystals having the regular crystal forms such as a cube, octahedron or tetradecahedron, the grains having an irregular crystal system such as a globular crystal system, the grains comprising imperfect crystals such as a twinned crystal, or the grains having the complex of the above-mentioned crystals. The grain size of the silver halide grains are to be not smaller than about 0.1 μm. An emulsion may be typified when at least about 95 wt % of the silver halide grains thereof have each a grain size within ±40% of the average grain size of the whole grain. In the invention, to be more concrete, it is allowed to use any emulsion of which an average grain size within the range of about 0.25 to 2 μm and at least about 95% by weight or at least about 95% by number of the silver halide grains have each a grain size within ±20% of the average grain size.

It is also allowed to apply tabular shaped grains having each an aspect ratio of not less than about 5 to the invention. Such tabular shaped grains can readily be prepared in the preparation processes disclosed in, for example, Gutoff, 'Photographic Science and Engineering', Vol. 14, pp. 248-257, 1970; U.S. Pat. Nos. 4,434,226, 4,414,310, 4,433,048 and 4,439,520; and British Patent No. 2,112,157. As for the emulsions ordinarily applicable to the invention, those subjected to a physical or chemical ripening treatment and a spectral sensitization may be used. The additives applicable to the above-mentioned treating courses are detailed in, for example, Research Disclosure Nos. 17643 and 18716, respectively. The known photographic additives applicable to the invention are also exemplified in the above-given Research Disclosures.

As for the supports applicable to the invention, any one applicable to photographic light sensitive materials may be used. However, they include, typically, those made of a cellulose acetate film, a polyvinyl acetate film and a polyethylene terephthalate film. Besides the above, a flexible supports such as a paper-made support can also be used.

The color developers applicable to the photographic light sensitive materials of the invention have each the same composition as those of the ordinary color developers each containing an aromatic primary amine developing agent.

Such a color developer can be contained with the other compounds for the components of the well known developers, besides the above additives. For example, alkalizers and buffers, such as caustic soda, caustic potash, sodium carbonate, potassium carbonate, tertiary sodium phosphate or tertiary potassium phosphate, potassium metaborate, and borax, may be used independently or in combination.

The above-mentioned color developers may each be added with a sulfite (such as sodium sulfite and sodium bisulfite) and hydroxylamine, which are ordinarily applicable as a preservative.

If required, any desired development accelerator can be added into the color developers.

After completing a color development, a photographic emulsion layers are ordinarily bleached. The bleaching treatment may be carried out either at the same time when carrying out a fixing treatment or by separating the bleaching treatment from the fixing treatment. As for the bleaching agents, potassium ferricyanide, iron (III) sodium ethylenediaminetetraacetate and iron (III) ammonium ethylenediaminetetraacetate are particularly useful. Besides, iron (III) aminopolycarboxylic acid complex is usefully applicable not only to an independent bleaching solution but also to a monobath type bleach-fixer.

The bleaching agents or the bleach-fixers may be added with a variety of additives including, for example, the bleaching accelerators disclosed in U.S. Pat. Nos. 3,042,520 and 3,241,966; and Japanese Patent Examined Publication Nos. 45-8506/1970 and 45-8836/1970.

As for the fixers applicable to fixing baths, an ammonium, sodium or potassium salt of thiosulfuric acid may be used in an amount of the order within the range of 30 g/liter to 200 g/liter. Besides the above, a pH buffer such as a sulfite, acetate, borate, phosphate or carbonate may also be added therein. The pH values of the fixers are within the range of 3 to 10 and, preferably, 5 to 9.

EXAMPLES

Some typical examples of the invention will now be detailed below. It is, however, to be understood that the embodiments of the invention shall not be limited thereto.

In every example given below, the amounts of the materials added into the photographic light sensitive materials are expressed in terms of grams per sq. meter unless otherwise expressly stated. The amounts of silver halides and colloidal silver are expressed in terms of the silver contents thereof, and the amounts of the sensitizing dyes are expressed in terms of mols per mol of the silver used.

EXAMPLE 1

A multilayered silver halide color photographic light sensitive material (Sample 1) was prepared in such a manner that each of the layers having the following composition was coated over a triacetyl cellulose film support in order from the support side.

Sample 1 (For Comparison)

| Layer 1: An antihalation layer (HC) | |
|---|---|
| Black colloidal silver | 0.15 |
| UV absorbent (UV-1) | 0.20 |
| Colored coupler (CC-1) | 0.02 |
| High boiling solvent (Oil-1) | 0.20 |

| -continued | |
|---|---|
| High boiling solvent (Oil-2) | 0.20 |
| Gelatin | 1.6 |
| Layer 2: An interlayer (IL-1) | |
| Gelatin | 1.3 |
| Layer 3: A low speed red sensitive emulsion layer (R-L) | |
| Silver iodobromide emulsion (Em-1) | 0.4 |
| Silver iodobromide emulsion (Em-2) | 0.3 |
| Sensitizing dye (S-1) | $3.2 \times 10^{-4}$ (mol/mol of silver) |
| Sensitizing dye (S-2) | $3.2 \times 10^{-4}$ (mol/mol of silver) |
| Sensitizing dye (S-3) | $0.2 \times 10^{-4}$ (mol/mol of silver) |
| Cyan coupler (C-1) | 0.50 |
| Cyan coupler (C-2) | 0.13 |
| Colored cyan coupler (CC-1) | 0.07 |
| DIR compound (D-1) | 0.016 |
| High boiling solvent (Oil-1) | 0.55 |
| Additive (SC-1) | 0.003 |
| Gelatin | 1.0 |
| Layer 4: A high speed red sensitive emulsion layer (R-H) | |
| Silver iodobromide emulsion (Em-3) | 0.9 |
| Sensitizing dye (S-1) | $1.7 \times 10^{-4}$ (mol/mol of silver) |
| Sensitizing dye (S-2) | $1.6 \times 10^{-4}$ (mol/mol of silver) |
| Sensitizing dye (S-3) | $0.1 \times 10^{-4}$ (mol/mol of silver) |
| Cyan coupler (C-2) | 0.23 |
| Colored cyan coupler (CC-1) | 0.03 |
| DIR compound (D-1) | 0.02 |
| High boiling solvent (Oil-1) | 0.25 |
| Additive (SC-1) | 0.003 |
| Gelatin | 1.0 |
| Layer 5: An interlayer (IL-2) | |
| Gelatin | 0.8 |
| Layer 6: A low speed green sensitive emulsion layer (G-L) | |
| Silver iodobromide emulsion (Em-1) | 0.6 |
| Silver iodobromide emulsion (Em-2) | 0.2 |
| Sensitizing dye (S-4) | $6.7 \times 10^{-4}$ (mol/mol of silver) |
| Sensitizing dye (S-5) | $0.8 \times 10^{-4}$ (mol/mol of silver) |
| Magenta coupler (M-1) | 0.17 |
| Magenta coupler (M-2) | 0.43 |
| Colored magenta coupler (CM-1) | 0.10 |
| DIR compound (D-2) | 0.02 |
| High boiling solvent (Oil-2) | 0.70 |
| Additive (SC-1) | 0.003 |
| Gelatin | 1.0 |
| Layer 7: A high speed green sensitive emulsion layer (G-H) | |
| Silver iodobromide emulsion (Em-3) | 0.9 |
| Sensitizing dye (S-6) | $1.1 \times 10^{-4}$ (mol/mol of silver) |
| Sensitizing dye (S-7) | $2.0 \times 10^{-4}$ (mol/mol of silver) |
| Sensitizing dye (S-8) | $0.3 \times 10^{-4}$ (mol/mol of silver) |
| Magenta coupler (M-1) | 0.03 |
| Magenta coupler (M-2) | 0.13 |
| Colored magenta coupler (CM-1) | 0.04 |
| DIR compound (D-2) | 0.004 |
| High boiling solvent (Oil-2) | 0.35 |
| Additive (SC-1) | 0.003 |
| Gelatin | 1.0 |
| Layer 8: A yellow filter layer (YC) | |
| Yellow colloidal silver | 0.1 |
| Additive (HS-1) | 0.07 |
| Additive (HS-2) | 0.07 |
| Additive (SC-2) | 0.12 |
| High boiling solvent (Oil-2) | 0.15 |

| -continued | |
|---|---|
| Gelatin | 1.0 |
| Layer 9: A low speed blue sensitive emulsion layer (B-L) | |
| Silver iodobromide emulsion (Em-1) | 0.25 |
| Silver iodobromide emulsion (Em-2) | 0.25 |
| Sensitizing dye (S-9) | $5.8 \times 10^{-4}$ (mol/mol of silver) |
| Yellow coupler (Y-1) | 0.60 |
| Yellow coupler (Y-2) | 0.32 |
| DIR compound (D-1) | 0.009 |
| High boiling solvent (Oil-2) | 0.18 |
| Additive (SC-1) | 0.004 |
| Gelatin | 1.3 |
| Layer 10: A high speed blue sensitive emulsion layer (B-H) | |
| Silver iodobromide emulsion (Em-4) | 0.5 |
| Sensitizing dye (S-10) | $3.0 \times 10^{-4}$ (mol/mol of silver) |
| Sensitizing dye (S-11) | $1.2 \times 10^{-4}$ (mol/mol of silver) |
| Yellow coupler (Y-1) | 0.18 |
| Yellow coupler (Y-2) | 0.10 |
| High boiling solvent (Oil-2) | 0.05 |
| Additive (SC-1) | 0.002 |
| Gelatin | 1.0 |
| Layer 11: The 1st protective layer (PRO-1) | |
| Silver iodobromide emulsion (Em-5) | 0.3 |
| UV absorbent (UV-1) | 0.07 |
| UV absorbent (UV-2) | 0.1 |
| Additive (HS-1) | 0.2 |
| Additive (HS-2) | 0.1 |
| High boiling solvent (Oil-1) | 0.07 |
| High boiling solvent (Oil-3) | 0.07 |
| Gelatin | 0.8 |
| Layer 12: The 2nd protective layer (PRO-2) | |
| An alkali-soluble matting agent, (with an average particle size of 2 μm) | 0.13 |
| Polymethyl methacrylate, (with an average particle size of 3 μm) | 0.02 |
| Lubricant (WAX-1) | 0.04 |
| Charge controller (SU-1) | 0.004 |
| Charge controller (SU-2) | 0.02 |
| Gelatin | 0.5 |

Each of the layers was suitably added by coating said SU-4, dispersing said SU-3, layer hardeners H-1 and H-2, stabilizer ST-1, anticeptic DI-1, antifoggants AF-1 and AF-2, and dyes AI-1 and AI-2, as well as the above-given compositions.

All the emulsions each applied to the above-mentioned sample were the following internally high iodide containing and monodisperse type emulsions:

Em-1: Comprises octahedral grains having an average AgI content of 7.5 mol % and a grain size of 0.55 μm;

Em-2: Comprises octahedral grains having an average AgI content of 2.5 mol % and a grain size of 0.36 μm;

Em-3: Comprises octahedral grains having an average AgI content of 8.0 mol % and a grain size of 0.84 μm;

Em-4: Comprises octahedral grains having an average AgI content of 8.5 mol % and a grain size of 1.02 μm; and Em-5: Comprises octahedral grains having an average AgI content of 2.0 mol % and a grain size of 0.08 μm.

Compounds Applied to Example 1

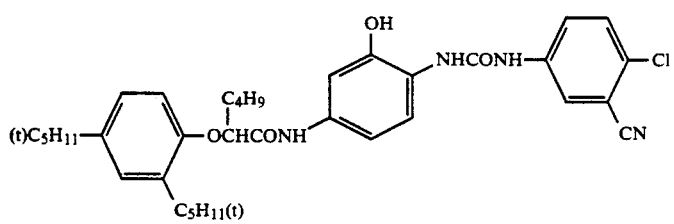 C-1
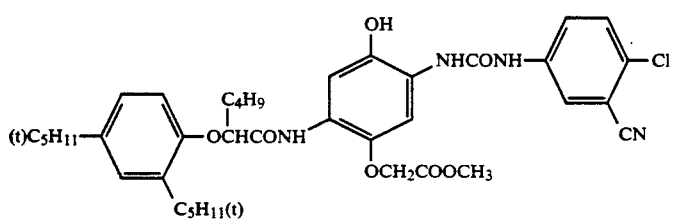 C-2
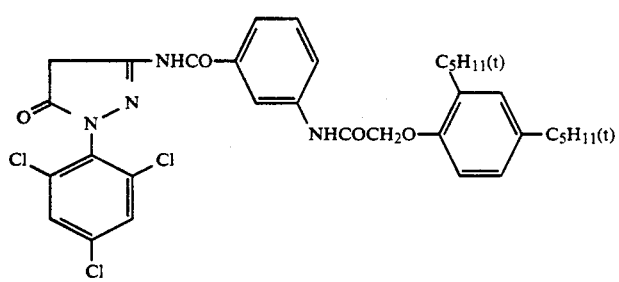 M-1
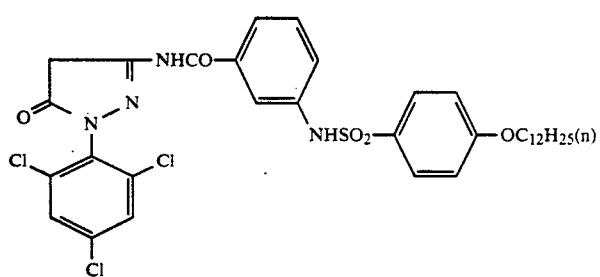 M-2
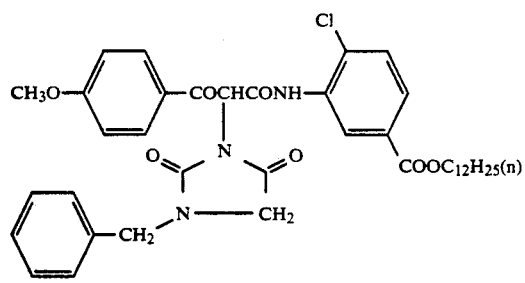 Y-1
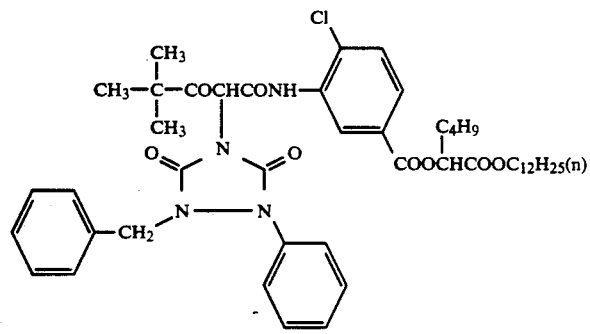 Y-2

CC-1
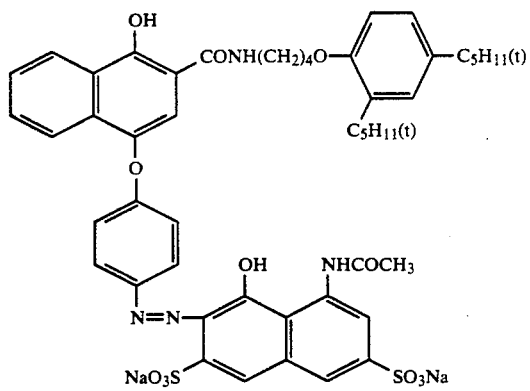
CM-1
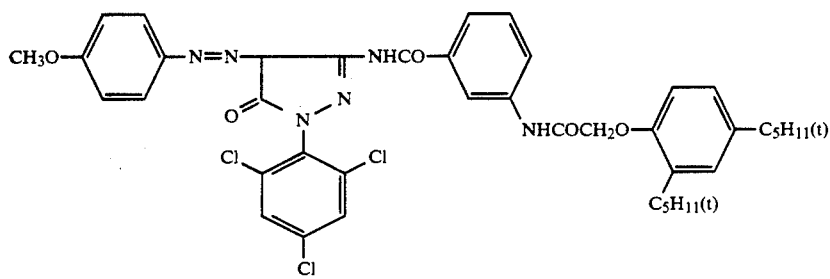
D-1
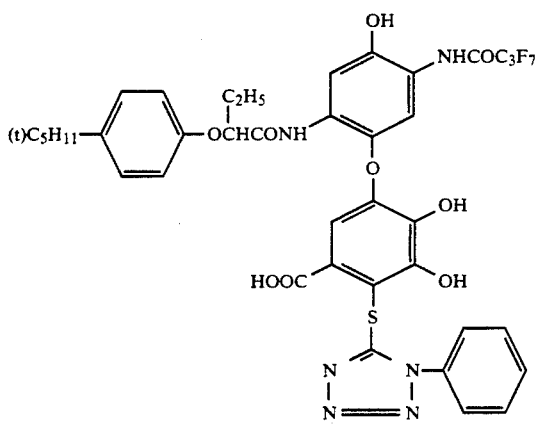
(Compound given in Japanese Patent O.P.I.Publication No. 61-233741)
D-2
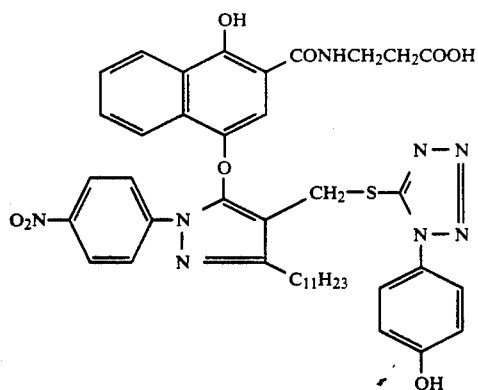
UV-1
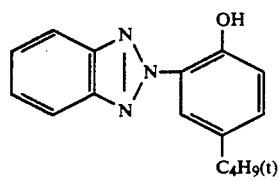

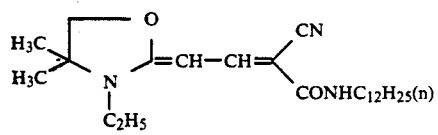 UV-2
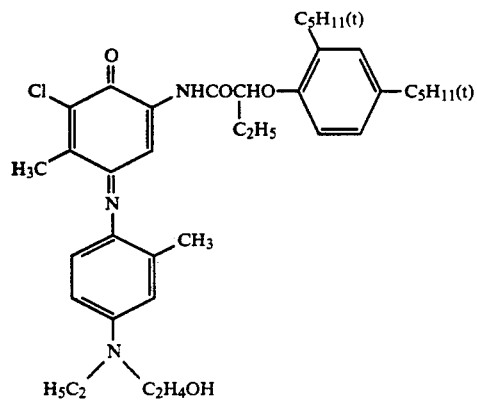 F-1
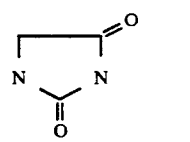 HS-1
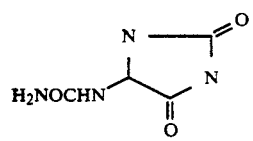 HS-2
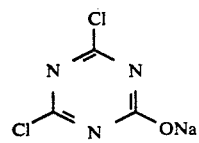 H-1
[(CH$_2$=CHSO$_2$CH$_2$)$_3$CCH$_2$SO$_2$CH$_2$CH$_2$]$_2$NCH$_2$CH$_2$SO$_3$K  H-2
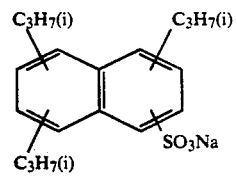 SU-3 (Alkanol XC)
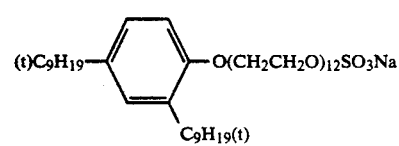 SU-2
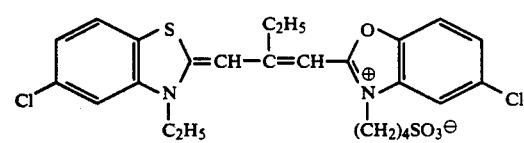 S-1
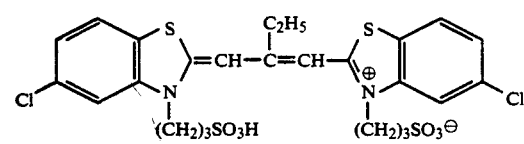 S-2

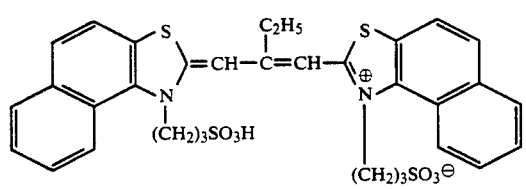
S-3
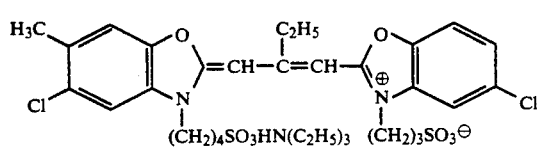
S-4
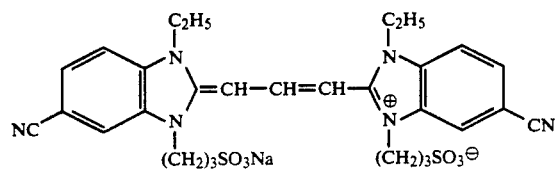
S-5
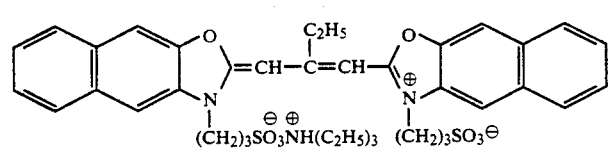
S-6
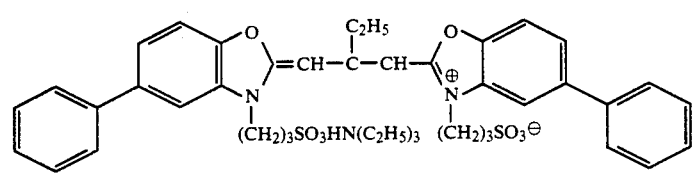
S-7
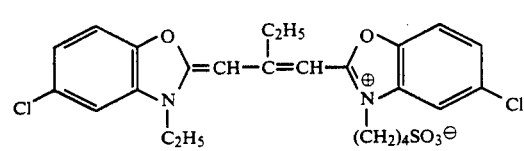
S-8
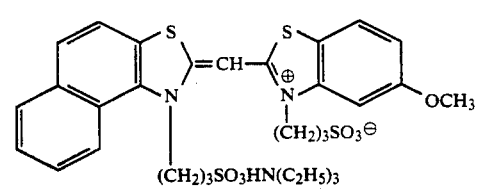
S-9
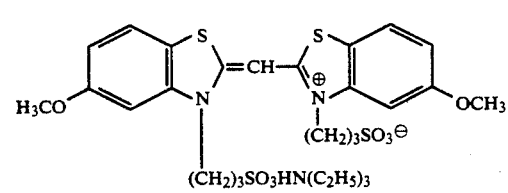
S-10
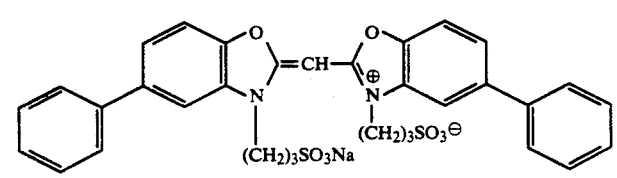
S-11
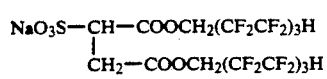
SU-1

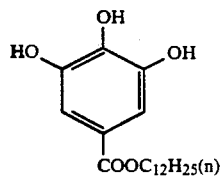
SC-1
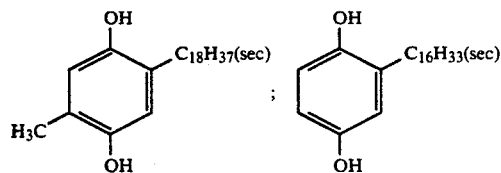
Mixture (2:3)
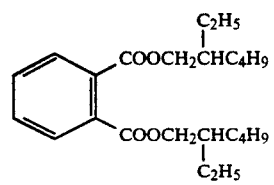
Oil-1
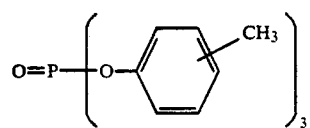
Oil-2
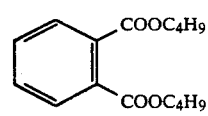
Oil-3
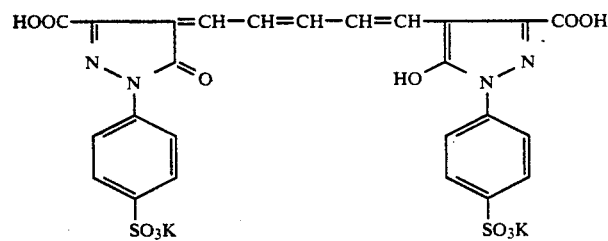
AI-1
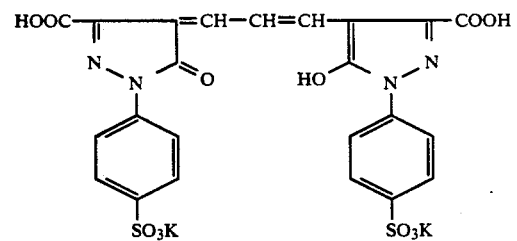
AI-2
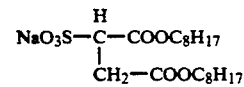
SU-4
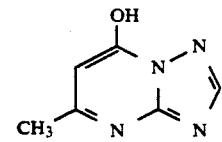
ST-1

Mixture of

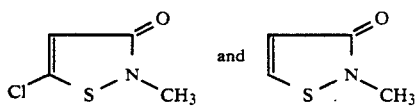
and

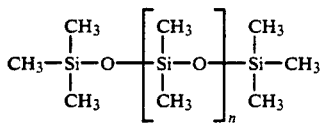

$\overline{MW}$: 30,000

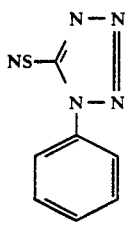

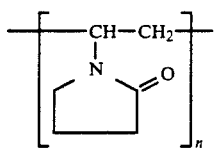

$\overline{MW}$: 9,000

DI-1

WAX-1

AF-1

AF-2

Further, Samples 2 through 5 were each prepared in such a manner that each of DIR compound (D-1) contained in Layers 3 and 4 of the foregoing Sample 1 was replaced by those in the equivalent mols as shown in The following Table 1.

The resulting Samples 1 through 8 were each exposed to white light through a wedge and they were developed. On the other hand, a part of Samples 1 through 8 were allowed to stand for 7 days under the conditions of 55° C. and 20%RH and they were developed in the same procedures as mentioned above. The photosensitive speeds and fog production of the samples were measured. The results thereof are shown in Table-1.

Besides the above, the image sharpness of each sample was also measured. Upon obtaining the MTF values of the dye images in terms of 30 lines/mm, the sharpness of each sample is expressed by a value relative to that of Sample 1 (which is regarded as a control value of 100).

TABLE 1

| Sample No. | DIR compound of layers 3,4 | Unprocessed | | 7 days-aging at 55° C., 20% RH | | |
| --- | --- | --- | --- | --- | --- | --- |
| | | Specific speed | Fog | Specific speed | Fog | Sharpness |
| 1 (Comparison) | D-1 | 99 | 0.15 | 91 | 0.31 | 101 |
| 2 (Comparison) | D-2 | 101 | 0.16 | 92 | 0.29 | 99 |
| 3 (Invention) | (1) | 102 | 0.14 | 99 | 0.20 | 112 |
| 4 (Invention) | (2) | 98 | 0.15 | 98 | 0.21 | 110 |
| 5 (Invention) | (5) | 101 | 0.15 | 99 | 0.21 | 101 |
| 6 (Invention) | (9) | 100 | 0.15 | 95 | 0.23 | 107 |
| 7 (Invention) | (17) | 99 | 0.13 | 94 | 0.22 | 108 |

TABLE 1-continued

| 8 (Invention) | (28) | 101 | 0.14 | 99 | 0.20 | 112 |

D-3

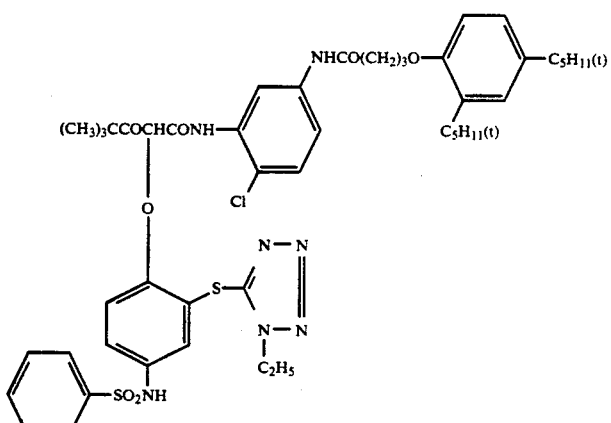

(Compound given in Japanese Patent O.P.I. Publication No. 60-185950/1985)

Processing steps (at 38° C.)

| Color developing | 3 min. 15 sec. |
|---|---|
| Bleaching | 6 min. 30 sec. |
| Washing | 3 min. 15 sec. |
| Fixing | 6 min. 30 sec. |
| washing | 3 min. 15 sec. |
| Stabilizing | 1 min. 30 sec. |
| Drying | |

The following compositions of the processing solutions were used in the above-given processing steps.

| [Color developer] | |
|---|---|
| 4-amino-3-methyl-N-ethyl-N-($\beta$-hydroxyethyl)-aniline.sulfate | 4.75 g |
| Sodium sulfite, anhydrous | 4.25 g |
| Hydroxylamine.½ sulfate | 2.0 g |
| Potassium carbonate, anhydrous | 37.5 g |
| Sodium bromide | 1.3 g |
| Trisodium.nitrilotriacetate, (monohydrate) | 2.5 g |
| Potassium hydroxide | 1.0 g |
| Add water to make | 1 liter |
| Adjust pH with potassium hydroxide to be | pH = 10.0 |
| [Bleaching solution] | |
| Iron (III) ammonium ethylenediaminetetraacetate | 100 g |
| Ammonium ethylenediaminetetraacetate | 10.0 g |
| Ammonium bromide | 150.0 g |
| Glacial acetic acid | 10.0 ml |
| Add water to make | 1 liter |
| Adjust pH with aqueous ammonia to be | pH = 6.0 |
| [Fixing solution] | |
| Ammonium thiosulfate (in an aqueous 50% solution) | 162 ml |
| Sodium sulfite, anhydrous | 12.4 g |
| Add water to make | 1 liter |
| Adjust pH with acetic acid to be | pH = 6.5 |
| [Stabilizing solution] | |
| Formalin (in an aqueous 37% solution) | 1.5 ml |
| Koniducks (manufactured by Konica Corp.) | 7.5 ml |
| Add water to make | 1 liter |

It can be found out from Table-1 that each of the samples prepared in accordance with the invention greatly improved in image sharpness and reduced the fogginess produced by heat in storage and, further prevented the photosensitive speeds from lowering.

EXAMPLE 2

A control sample was prepared by applying a multilayer coating onto a triacetate film base in the following order:

(1) A red sensitive silver iodobromide emulsion layer containing 0.5 g of cyan coupler C-2, 2.4 g of gelatin and 1.6 g of silver halide;

(2) An interlayer containing 0.5 g of gelatin and 0.1 g of 2,5-di-t-octyl hydroquinone;

(3) A blue sensitive silver iodobromide emulsion layer containing 1.70 g of yellow coupler Y-1, 2.4 g of gelatin and 1.6 g of silver halide; and (4) A protective layer comprising 0.8 g of gelatin.

After then, the five kinds of Samples 6, 7, 8, 9 and 10 were prepared, respectively, by adding the following DIR compounds in the amounts shown in Table-2 into the third layer containing yellow coupler out of the component layers of the above-described multilayer coated light sensitive material for control.

The resulting samples were each divided into two parts, respectively. With each of the resulting samples, one of the two parts was exposed to white light through a wedge, and the other parts was exposed to red light through a wedge.

Each of the exposed sample parts was developed in the same procedures as in Example 1.

With the developed samples, the gamma values thereof were obtained from the characteristic curve of the cyan dye produced by making a color development, and Table-2 shows the values ($\gamma R/\gamma W$) obtained by dividing the gamma ($\gamma R$) obtained in red light exposure by the gamma ($\gamma W$) obtained in white light exposure.

TABLE 2

| Sample No. | DIR compound | Amount added (mol/m$^2$) | $\gamma R/\gamma W$ |
|---|---|---|---|
| 9 (Comparison) | D-4 | $3.0 \times 10^{-4}$ | 1.10 |
| 10 (Comparison) | D-5 | $3.0 \times 10^{-4}$ | 1.22 |

TABLE 2-continued

| Sample No. | DIR compound | Amount added (mol/m²) | $\gamma_R/\gamma_W$ |
|---|---|---|---|
| 11 (Invention) | (13) | $3.0 \times 10^{-4}$ | 1.53 |
| 12 (Invention) | (14) | $3.0 \times 10^{-4}$ | 1.54 |
| 13 (Invention) | (16) | $3.0 \times 10^{-4}$ | 1.50 |
| 14 (Invention) | (12) | $3.0 \times 10^{-4}$ | 1.45 |

D-4

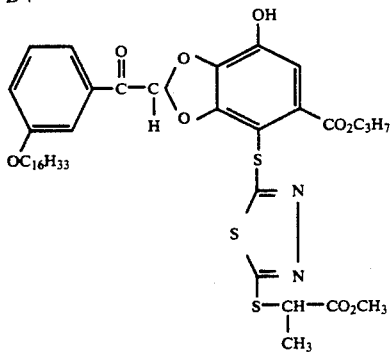

(Compound given in Japanese Patent O.P.I. Publication No. 1-164942/1989)

D-5

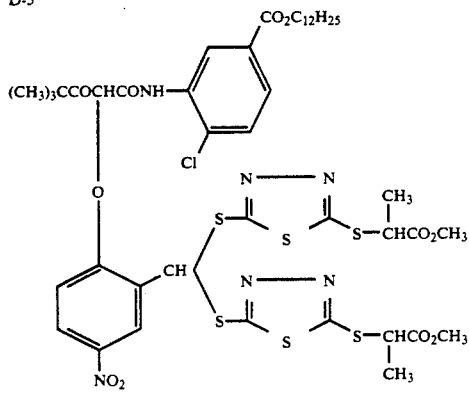

(Compound given in Japanese Patent O.P.I. Publication No. 1-164942/1989)

As is obvious from Table-2, it can be recognized that the compounds of the invention are so great in $\gamma R/\gamma W$ value that the greater interlayer effects can be enjoyed as compared to the cases where the conventional DIR couplers are used.

EXAMPLE 3

A comparative sample 14 of multilayered color light sensitive material was prepared in such a manner that the layers having the following composition were each coated over a subbed cellulose triacetate film support in order from the support side. The amounts of the component materials coated are expressed in terms of g/m², except that the amounts of silver halides coated are expressed in terms of the silver contents thereof.

| Layer 1: (An antihalation layer) | |
|---|---|
| Black colloidal silver | 0.24 |
| UV absorbent U-1 | 0.14 |
| UV absorbent U-2 | 0.072 |
| UV absorbent U-3 | 0.072 |
| UV absorbent U-4 | 0.072 |
| High boiling solvent O-1 | 0.31 |
| High boiling solvent O-2 | 0.098 |
| Poly N vinylpyrrolidone, (having an average molecular weight of several hundred thousand) | 0.15 |
| Gelatin | 2.02 |
| Layer 2: (An interlayer) | |
| Dye D-1 | 0.011 |
| High boiling solvent O-3 | 0.011 |
| Gelatin | 1.17 |
| Layer 3: (A low speed red sensitive layer) | |
| Silver iodobromide emulsion, spectrally sensitized with red sensitizing dyes S-1 and S-2 (containing a silver iodide: 3.0 mol %, 0.57 μm) | 0.056 |
| Silver iodobromide emulsion, spectrally sensitized with red sensitizing dyes S-1 and S-2 (containing a silver iodide: 3.0 mol %, 0.27 μm) | 0.504 |
| Coupler C-1 | 0.37 |
| High boiling solvent O-2 | 0.093 |
| Poly N vinylpyrrolidone | 0.074 |
| Gelatin | 1.35 |
| Layer 4: (A high speed red sensitive layer) | |
| Silver iodobromide emulsion, spectrally sensitized with red sensitizing dyes S-1 and S-2 (containing a silver iodide: 3.0 mol %, 0.57 μm) | 0.71 |
| Coupler C-1 | 0.85 |
| High boiling solvent O-2 | 0.21 |
| Poly N vinylpyrrolidone | 0.093 |
| Gelatin | 1.56 |
| Layer 5: (An interlayer) | |
| Color mixture inhibitor AS-1 | 0.20 |
| High boiling solvent O-3 | 0.25 |
| Matting agent MA-1 | 0.0091 |
| Gelatin | 1.35 |
| Layer 6: (A low speed green sensitive layer) | |
| Silver iodobromide emulsion, spectrally sensitized with green sensitizing dyes S-3 and S-4 (containing a silver iodide: 3.0 mol %, 0.60 μm) | 0.056 |
| Silver iodobromide emulsion, spectrally sensitized with green sensitizing dyes S-3 and S-4 (containing a silver iodide: 3.0 mol %, 0.27 μm) | 0.51 |
| Coupler M-1 | 0.31 |
| Coupler M-2 | 0.076 |
| High boiling solvent O-3 | 0.059 |
| Poly N vinylpyrrolidone | 0.074 |
| Gelatin | 1.29 |
| Layer 7: (A high speed green sensitive layer) | |
| Silver iodobromide emulsion, spectrally sensitized with green sensitizing dyes S-3 and S-4 (containing a silver iodide: 3.0 mol %, 0.60 μm) | 0.83 |
| Silver iodobromide emulsion, spectrally sensitized with green sensitizing dyes S-3 and S-4 (containing a silver iodide: 3.0 mol %, 0.27 μm) | 0.092 |
| Coupler M-1 | 0.80 |
| Coupler M-2 | 0.19 |
| Color mixture inhibitor AS-1 | 0.055 |
| High boiling solvent O-3 | 0.16 |
| Poly N vinylpyrrolidone | 0.12 |
| Gelatin | 1.91 |
| Layer 8: (An interlayer) | |
| Gelatin | 0.90 |
| Layer 9: (A yellow filter layer) | |
| Yellow colloidal silver | 0.11 |
| Color mixture inhibitor AS-1 | 0.068 |
| High boiling solvent O-3 | 0.085 |
| Matting agent MA-1 | 0.012 |
| Gelatin | 0.68 |
| Layer 10: (A low speed blue sensitive layer) | |
| Silver iodobromide emulsion, spectrally sensitized with blue sensitizing dyes S-5 and S-6 (containing a silver iodide: | 0.24 |

| -continued | |
|---|---|
| 3.0 mol %, 0.85 μm) | |
| Silver iodobromide emulsion, spectrally sensitized with blue sensitizing dyes S-5 and S-6 (containing a silver iodide: 3.0 mol %, 0.42 μm) | 0.30 |
| Silver iodobromide emulsion, spectrally sensitized with blue sensitizing dyes S-5 and S-6 (containing a silver iodide: 3.0 mol %, 0.27 μm) | 0.060 |
| Coupler Y-1 | 0.86 |
| Image stabilizer G-1 | 0.012 |
| High boiling solvent O-3 | 0.22 |
| Poly N vinylpyrrolidone | 0.078 |
| Compound F-1 | 0.020 |
| Compound F-2 | 0.040 |
| Gelatin | 1.50 |
| Layer 11: (A high speed blue sensitive layer) | |
| Silver iodobromide emulsion, spectrally sensitized with blue sensitizing dyes S-5 and S-6 (containing a silver iodide: 3.0 mol %, 0.85 μm) | 0.79 |
| Coupler Y-1 | 1.24 |
| Image stabilizer G-1 | 0.017 |
| High boiling solvent O-3 | 0.31 |
| Poly N vinylpyrrolidone | 0.10 |
| Compound F-1 | 0.039 |
| Compound F-2 | 0.077 |
| Gelatin | 1.73 |
| Layer 12: (Protective layer 1) | |
| A non-light-sensitive, fine-grained silver iodobromide (containing silver iodide: 1.0 mol %, 0.08 μm) | 0.075 |
| UV absorbent U-1 | 0.048 |
| UV absorbent U-2 | 0.024 |
| UV absorbent U-3 | 0.024 |
| UV absorbent U-4 | 0.024 |
| Dye D-2 | 0.064 |
| Dye D-3 | 0.13 |
| High boiling solvent O-1 | 0.13 |
| High boiling solvent O-2 | 0.13 |
| Compound F-1 | 0.075 |
| Compound F-2 | 0.15 |
| Gelatin | 1.2 |
| Layer 13: (Protective layer 2) | |
| Lubricant WAX-1 | 0.041 |
| Matting agent MA-2 | 0.0090 |
| Matting agent MA-3 | 0.051 |
| Surfactant SU-1 | 0.0036 |
| Gelatin | 0.55 |

Besides the above compositions, gelatin hardeners H-1, H-2 and H-3, water-soluble dyes AI-1, AI-2 and AI-3, antimold DI-1, stabilizer ST-1 and antifoggant AF-1 were each suitably added into the sample so as to meet the requirements.

Compounds Applied to Example 3

Sensitizing Dyes

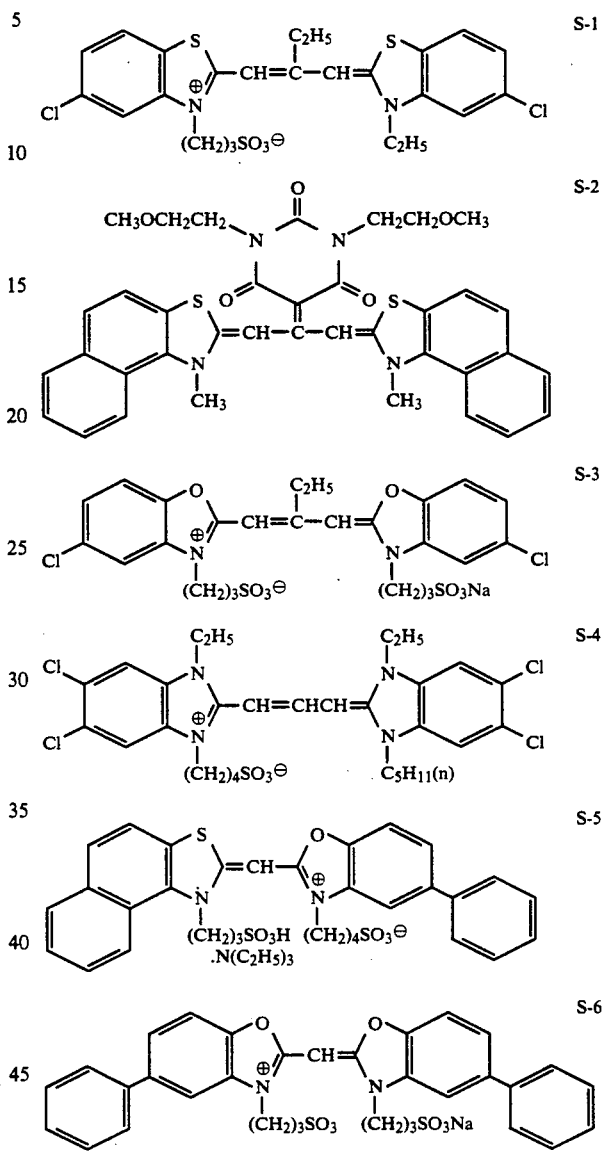

Couplers

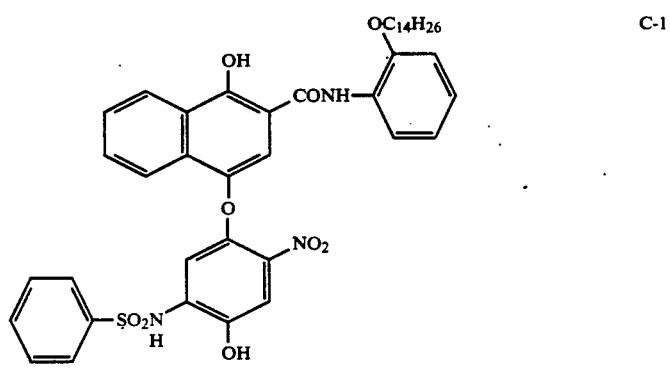

-continued

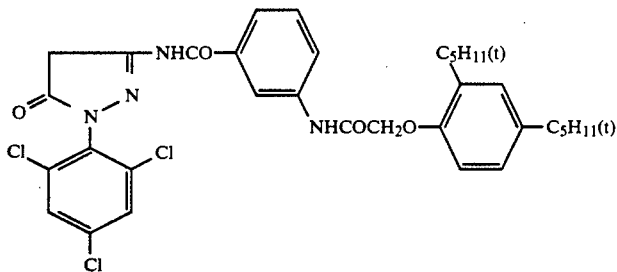
M-1

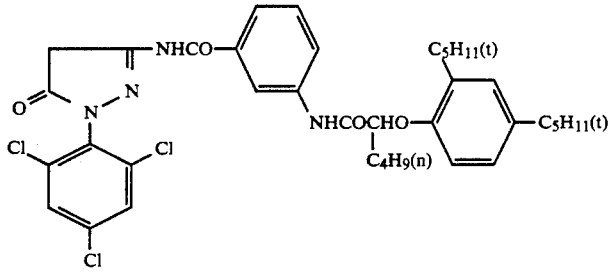
M-2

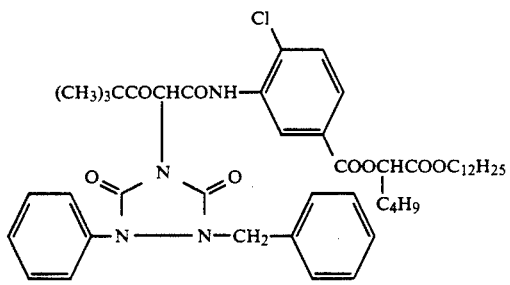
Y-1

Compounds

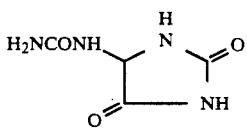
F-1

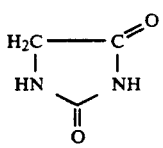
F-2

Matting Agents

| MA-1 | Collodial silica particles (having an average particle size of 3.5 μm) |
|---|---|
| MA-2 | Polymethyl methacrylate particles (having an average particle size of 3.0 μm) |
| MA-3 | $\{CH_2-\underset{COOCH_3}{\underset{|}{\overset{CH_3}{\overset{|}{C}}}}\}_l\{CH_2-\underset{COOC_2H_5}{\underset{|}{\overset{CH_3}{\overset{|}{C}}}}\}_m\{CH_2-\underset{COOH}{\underset{|}{\overset{CH_3}{\overset{|}{C}}}}\}_n$ (l:m:n = 30:30:40) |

UV Absorbents

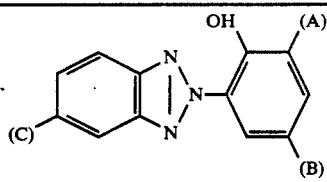

| | A | B | C |
|---|---|---|---|
| U-1 | —H | —C$_4$H$_9$(t) | —H |
| U-2 | —C$_4$H$_9$(t) | —C$_4$H$_9$(t) | —H |
| U-3 | —C$_4$H$_9$(t) | —CH$_3$ | —Cl |
| U-4 | —C$_4$H$_9$(t) | —C$_4$H$_9$(t) | —Cl |

High Boiling Solvents

O-1 di-2-dethylhexyl phthalate
O-2 di-butyl phthalate
O-3 tricresyl phosphate

Dyes

D-1: [structure: chloro-methyl-quinone imine dye with NHCOCH(C2H5)O-aryl(2,4-di-t-C5H11) group and N(C2H5)(C2H4OH)-tolyl group]

D-2: [structure: 1-ethylpyrrolidin-2-ylidene-CH=CH-C(CN)(CONHC12H25(n))]

D-3: [structure: 4,4-dimethyl-3-ethyl-oxazolidinone with =CH—CH=C(CN)CONHC12H25(n)]

Color Mixture Inhibitor

A mixture (2:3) of

[2,5-dihydroxy-4-methyl-1-(sec-C18H37)benzene] and [2,5-dihydroxy-1-(sec-C16H33)benzene] — AS-1

Image Stabilizer

G-1: 3,4,5-trihydroxybenzoic acid n-dodecyl ester (COOC12H25(n))

Lubricant

WAX-1: $CH_3-Si(CH_3)_2-O-[Si(CH_3)_2-O]_n-Si(CH_3)_3$ (Average molecular weight: 30,000)

Surfactant

SU-1: $NaO_3S-CH(COOCH_2(CF_2CF_2)_3H)-CH_2COOCH_2(CF_2CF_2)_3H$

Hardeners

H-1: 2-(ONa)-4,6-dichloro-1,3,5-triazine

H-2: $[(CH_2=CHSO_2CH_2)_3CCH_2SO_2(CH_2)_2]_2N(CH_2)_2SO_3K$

H-3: $(CH_2=CH-SO_2CH_2)_2O$

Water-soluble Dyes

AI-1: [bis-pyrazolone pentamethine oxonol dye with p-SO3K phenyl groups]

AI-2: [bis-pyrazolone trimethine oxonol dye with p-SO3K phenyl groups]

-continued

AI-3

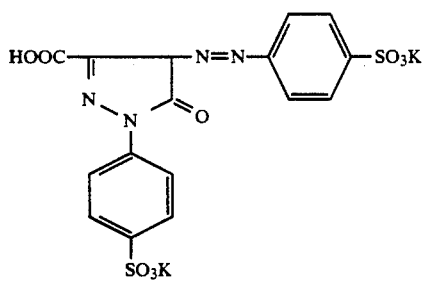

Antimold

A mixture of

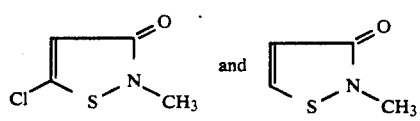

Stabilizer    Antifoggant

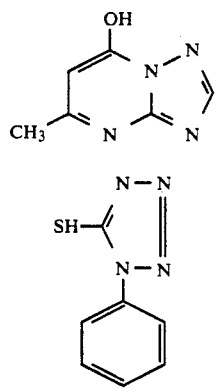

ST-1

AF-1

| Processing step | Processing time | Processing temperature |
|---|---|---|
| The 1st developing | 6 min. | 38° C. |
| Washing | 2 min. | 38° C. |
| Reversing | 2 min. | 38° C. |
| Color developing | 6 min. | 38° C. |
| Controlling | 2 min. | 38° C. |
| Bleaching | 6 min. | 38° C. |
| Fixing | 4 min. | 38° C. |
| Washing | 4 min. | 38° C. |
| Stabilizing | 1 min. | at ordinary temp. |
| Drying | | |

In the above-given processing steps, the compositions of the processing solutions used were as follows:

| The first developer | |
|---|---|
| Sodium tetrapolyphosphate | 2 g |
| Sodium sulfite | 20 g |
| Hydroquinone.monosulfonate | 30 g |
| Sodium carbonate (monohydrate) | 30 g |
| 1-phenyl-4-methyl-4-hydroxymethyl-3-pyrazolidone | 2 g |
| Potassium bromide | 2.5 g |
| Potassium thiocyanate | 1.2 g |
| Potassium iodide | 2 ml |
| (in an aqueous 0.1% solution) | |

-continued

| | |
|---|---|
| Add water to make | 1000 ml |
| Adjust pH to be | (pH = 9.60) |
| Reversal solution | |
| Hexasodium nitrilotrimethylene-sulfonate | 3 g |
| Stannous chloride (dihydrate) | 1 g |
| p-aminophenol | 0.1 g |
| Sodium hydroxide | 8 g |
| Glacial acetic acid | 15 ml |
| Add water to make | 1000 ml |
| Adjust pH to be | (pH = 5.75) |
| Color developer | |
| Sodium tetrapolyphosphate | 3 g |
| Sodium sulfite | 7 g |
| Tertiary sodium phosphate (dihydrate) | 36 g |
| Potassium bromide | 1 g |
| Potassium iodide (in a 0.1% solution) | 90 ml |
| Sodium hydroxide | 3 g |
| Citrazinic acid | 1.5 g |
| N-ethyl-N-$\beta$-methanesulfonamido-ethyl-3-methyl-4-aminoaniline.sulfate | 11 g |
| 2,2-ethylenedithiodiethanol | 1 g |
| Add water to make | 1000 ml |
| Adjust pH to be | (pH = 11.70) |
| Controlling solution | |
| Sodium sulfite | 12 g |
| Sodium ethylenediaminetetraacetate (dihydrate) | 8 g |
| Thioglycerol | 0.4 ml |
| Glacial acetic acid | 3 ml |
| Add water to make | 1000 ml |
| Adjust pH to be | (pH = 6.15) |
| Bleaching solution | |
| Sodium ethylenediaminetetraacetate (dihydrate) | 2 g |
| Iron (III) ammonium ethylene-diaminetetraacetate (dihydrate) | 120 g |
| Ammonium bromide | 100 g |
| Add water to make | 1000 ml |
| Adjust pH to be | (pH = 5.65) |
| Fixing solution | |
| Ammonium thiosulfate | 80 g |
| Sodium sulfite | 5 g |
| Sodium bisulfite | 5 g |
| Add water to make | 1000 ml |
| Adjust pH to be | (pH = 6.60) |
| Stabilizing solution | |
| Formalin (in a 37 wt % solution) | 5 ml |
| Koniducks (manufactured by Konica Corp.) | 5 ml |
| Add water to make | 1000 ml |

On the other hand, Samples 15 through 17 were each prepared by making use of the cyan couplers shown in the following Table-3 in place of cyan coupler C-1 used in Layers 3 and 4 of the foregoing multilayer-coated sample 14, in the same mols with each other cyan couplers, respectively. In the same manner as in Example 1, one parts each of the resulting samples 14 through 17 were allowed to stand for 7 days under the conditions of 55° C. and 20%RH, and the other parts each were kept untreated. Each of the two parts was exposed at the same time to white light through wedge, and the image sharpness of each sample was measured. Upon obtaining the MTF values of the dye images in terms of 30 lines/mm, the sharpness of each sample is expressed by a value relative to that of the untreated Sample 11 (which is regarded as a control value of 100).

TABLE 3

| Sample No. | Cyan couplers of Layers 3 and 4 | Image sharpness Untreated | Treated at 55° C. |
|---|---|---|---|
| 14 (Comparison) | C-1 | 100 | 89 |
| 15 (Comparison) | C-2 | 99 | 90 |
| 16 (Invention) | (21) | 105 | 103 |
| 17 (Invention) | (23) | 104 | 103 |

C-2

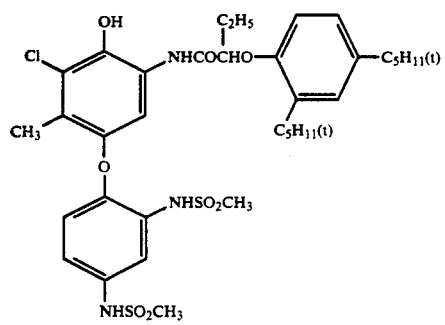

It can be proved from Table-3 that the compounds of the invention can remarkably reduce the image sharpness lowering produced by heat in preservation.

What is claimed is:

1. A silver halide photographic light sensitive material comprising:
a compound represented by formula I:

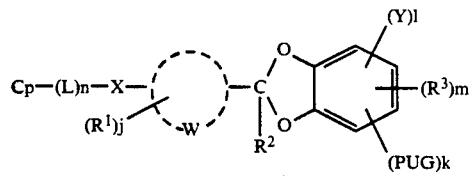

Formula I wherein, Cp represents a coupler residual group from which a hydrogen atom present in an active site is removed; L represents a linking group; n is an integer of 0 or 1; $R^1$, $R^2$ and $R^3$ each represent a hydrogen atom or a substituent; W represents an aromatic group having a 5- or 6-membered ring; j is an integer of 0 to 4; PUG represents a photographically useful qroup; l is an integer of 0 or 1; m and k are each an integer of 0 to 4, provided, 1+m+k is an integer of not more than 4; X represents a divalent coupling group; and Y represents a substituent substitutable with a benzene ring through a hetero atom.

2. The material of claim 1, wherein the PUG is a tetrazoly-5-thio, 1,3,4-thiadiazolyl-2-thio, 1,3,4- oxadiazolyl-2-thio, 1,3,4-triazolyl-2-thio, benzoimidazolyl-2-thio, benzoxazolyl-2-thio, benzothiazoly, benzimidazolyl or an imidazolylthio group, each of which may have a substituent.

3. The material of claim 1, wherein L is a linking group represented by formula XV or formula XVI:

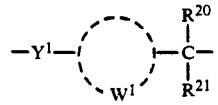

formula XV wherein $W^1$ represents a benzene ring or a naphthalene ring which may have a substituent; $Y^1$ represents —O—, —S—, or —$NR^{22}$— each coupled to the coupling position of a coupler residual group represented by Cp denoted in formula 1; $R^{20}$, $R^{21}$ and $R^{22}$ each represent a hydrogen atom, an alkyl or aryl group; and

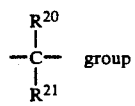 group is substituted to $Y^1$ in the ortho or para position so a to be coupled to X;

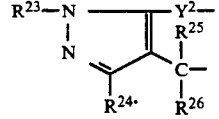

formula XVI wherein $Y^2$, $R^{25}$, and $R^{26}$ are each synonymous with $Y^1$, $R^{20}$ and $R^{21}$ each denoted in formula XV, respectively, $R^{23}$ represents a hydrogen atom, an alkyl, acyl, sulfonyl, alkoxycarbonyl, or a heterocyclic residual group; and $R^{24}$ represents a hydrogen atom, an alkyl, aryl, heterocyclic residual group, an alkoxy, amino, acylamino, sulfonylamino, carboxy, alkoxycarbonyl, carbamoyl, or a cyano group.

4. The material of claim 1, wherein $R^1$ and $R^3$ each represent a hydrogen atom, halogen atom, or an alkyl, aryl, heteroaryl, alkoxyl, amino, alkylamino, alkycarbamoyl, arycarbamoyl, acylamino, arylamino, ureido, sufonylamino, nitro, cyano, alkylsulfonyl, arylsulfonyl, alkoxycarbonyl, aryloxycarbonyl,alkoxysulfonyl, or aryloxysulfonyl group.

5. The material of claim 4, wherein $R^3$ represents a nitro, cyano, sulfamoyl, alkylsulfamoyl, arylsulfamoyl, carbamoyl, alkylcarbamoyl, arylcarbamoyl, alkyloxycarbonyl, aryloxycarbonyl, or carboxyl group.

6. The material of claim 1, wherein $R^2$ represents a hydrogen atom, an alkyl, aryl or acyl group.

7. The material of claim 1, wherein W represents a benzene, naphthalene, pyridine, pyrazole, imidazole, oxazole,thiazole, isoxazole, isothiazole, furan, thiophene, indole, benzofuran or benzothiophen group.

8. The material of claim 1, wherein Y represents a hydroxy, alkoxy, amino, alkylamino, sulfonylamino, acylamino, sulfamoylamino, alkylsulfamoylamino, or arylsulfamoylamino group.

9. The material of claim 1, wherein Y represents hydroxy group.

10. A silver halide photographic light sensitive material comprising:
a compound represented by formula XVII:

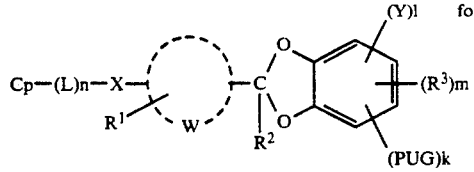

wherein

Cp represents a coupler residual group from which a hydrogen atom present in an active site is removed;

L represents a linking group; $R^1$ and $R^2$ each represent a hydrogen atom or a substituent; X represents an Oxygen atom, sulfur atom or a nitrogen containing divalent coupling group;

n is an integer of 0 or 1;

W is

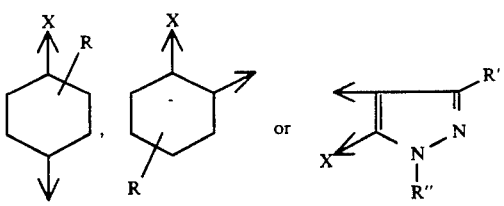

Wherein,

R and R' each represent an alkyl, aryl, acylamino, nitro, cyano, alkyloxycarbonyl, carbamoyl, or alkylsulfonylamino group; and R" represents an alkyl, aryl, or heteroaryl group; and Y is a hydroxyl group or a hydrogen atom; $R^3$ is COR'''' wherein R''' is $CH_3$ or $NHC_3H_7(i)$ wherein Y is a para position to PUG and $R^3$ is ortho positon to PUG;

PUG is

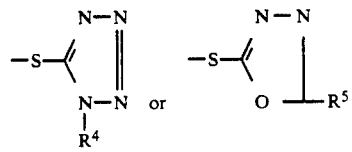

wherein $R^4$ is a phenyl, hydroxyphenyl, ethyl, or methylcarbonylphenyl group, and $R^5$ is a phenyl, methyl, ethyl, or propylcarboxymethyl group.

* * * * *

UNITED STATES PATENT AND TRADEMARK OFFICE
CERTIFICATE OF CORRECTION

PATENT NO. : 5,221,599
DATED : June 22, 1993
INVENTOR(S) : Eisaku Katoh et al.

It is certified that error appears in the above-indentified patent and that said Letters Patent is hereby corrected as shown below:

Claim 2, column 57, line 62, change "1,3,4- ox-" to --1,3,4,-ox---.

Claim 2, column 57, line 64, change "benzothiazoly" to --benzothiazolyl--.

Claim 3, column 58, second line above formula XVI change "so a to" to --so as to--.

Claim 4, column 58, line 46, change "aryloxycarbonyl,alkoxysulfonyl" to --aryloxycarbonyl, alkoxysulfonyl--.

Claim 5, column 58, line 50 and 51, change "alkylox-ycarbonyl," to --alkyloxy-carbonyl,--.

Claim 7, column 58, line 57, change "oxazole,thiazole," to --oxazole, thiazole,--.

Claim 10, column 60, line 17, change "COR'''" TO --COR' "--.

Claim 10, column 60, line 17, change "R'''" to --R'"--.

UNITED STATES PATENT AND TRADEMARK OFFICE
CERTIFICATE OF CORRECTION

PATENT NO. : 5,221,599
DATED : June 22, 1993
INVENTOR(S) : Eisaku Katoh et al.

It is certified that error appears in the above-indentified patent and that said Letters Patent is hereby corrected as shown below:

Claim 10, column 60, line 18, change "a" to --at--.

Signed and Sealed this

Sixth Day of September, 1994

Attest:

BRUCE LEHMAN

Attesting Officer     Commissioner of Patents and Trademarks